US011894115B2

(12) United States Patent
Stewart et al.

(10) Patent No.: US 11,894,115 B2
(45) Date of Patent: Feb. 6, 2024

(54) SPONGE COUNTING SYSTEM AND METHOD FOR ENSURING PROPER REMOVAL OF SURGICAL SPONGES FOLLOWING A MEDICAL PROCEDURE

(71) Applicant: Stryker Corporation, Kalamazoo, MI (US)

(72) Inventors: Brian Stewart, Ladera Ranch, CA (US); Michael Roux, Lake Forest, CA (US); Thomas Armentrout, Carlsbad, CA (US)

(73) Assignee: Stryker Corporation, Kalamazoo, MI (US)

(*) Notice: Subject to any disclaimer, the term of this patent is extended or adjusted under 35 U.S.C. 154(b) by 19 days.

(21) Appl. No.: 17/856,384

(22) Filed: Jul. 1, 2022

(65) Prior Publication Data

US 2022/0336072 A1 Oct. 20, 2022

Related U.S. Application Data

(63) Continuation of application No. 15/569,629, filed as application No. PCT/US2016/029324 on Apr. 26, 2016, now abandoned.

(Continued)

(51) Int. Cl.
*G16H 15/00* (2018.01)
*G16H 40/20* (2018.01)
(Continued)

(52) U.S. Cl.
CPC ............ *G16H 15/00* (2018.01); *A61B 90/08* (2016.02); *A61B 90/98* (2016.02); *G06Q 10/08* (2013.01);
(Continued)

(58) Field of Classification Search
CPC ........ G16H 15/00; G16H 40/20; G16H 10/60; G16H 40/40; A61B 90/08; A61B 90/98;
(Continued)

(56) References Cited

U.S. PATENT DOCUMENTS 5,931,824 A 8/1999 Stewart et al.
8,105,296 B2 1/2012 Morris et al.
(Continued)

FOREIGN PATENT DOCUMENTS

WO 2008033574 3/2008
WO 2008033574 A2 3/2008
(Continued)

OTHER PUBLICATIONS

Verna C. Gibbs MD, Therapeutic Packing, Vaginal Packing and Would Packing: HELP!!! It's all so confusing . . . 2013, No Thing Left Behind, Slides 1-59 (Year 2013) (Year: 2013).*
(Continued)

*Primary Examiner* — Paul Danneman
(74) *Attorney, Agent, or Firm* — Howard & Howard Attorneys PLLC

(57) ABSTRACT

A sponge counting system for maintaining an inventory of articles used during a medical or surgical procedure, where, in the event an article for which the status needs to be reconciled is left in a patient, the system generates a record that the article is in a partially reconciled state and when a subsequent procedure is performed, the scanner employed during the procedure has the records of the partially reconciled articles associated with the patient.

20 Claims, 20 Drawing Sheets

Related U.S. Application Data

(60) Provisional application No. 62/258,855, filed on Nov. 23, 2015, provisional application No. 62/153,100, filed on Apr. 27, 2015.

(51) Int. Cl.

| | | |
|---|---|---|
| *G16H 10/60* | (2018.01) | |
| *G16H 40/40* | (2018.01) | |
| *A61B 90/00* | (2016.01) | |
| *A61B 90/98* | (2016.01) | |
| *G16Z 99/00* | (2019.01) | |
| *G06Q 10/08* | (2023.01) | |
| *G06Q 10/0875* | (2023.01) | |
| *G06Q 10/30* | (2023.01) | |
| *G06K 19/07* | (2006.01) | |

(52) U.S. Cl.
CPC ......... *G06Q 10/0875* (2013.01); *G06Q 10/30* (2013.01); *G16H 10/60* (2018.01); *G16H 40/20* (2018.01); *G16H 40/40* (2018.01); *G16Z 99/00* (2019.02); *A61B 2090/0805* (2016.02); *G06K 19/0723* (2013.01); *Y02W 90/00* (2015.05)

(58) Field of Classification Search
CPC ............. A61B 2090/0805; G16Z 99/00; G06Q 10/08; G06Q 10/0875; G06Q 10/30; Y02W 99/00; G06K 19/0723
See application file for complete search history.

(56) References Cited

U.S. PATENT DOCUMENTS

| | | |
|---|---|---|
| 2007/0090788 A1 | 4/2007 | Hansford et al. |
| 2008/0237341 A1 | 10/2008 | Fleck et al. |
| 2010/0179822 A1 | 7/2010 | Reppas |
| 2013/0060577 A1 | 3/2013 | DeBusk et al. |
| 2016/0171262 A1 | 6/2016 | Fleck et al. |
| 2016/0371574 A1* | 12/2016 | Nguyen ............. G06K 17/0022 |
| 2018/0353256 A1 | 12/2018 | Stewart et al. |

FOREIGN PATENT DOCUMENTS

| | | |
|---|---|---|
| WO | 2014182701 | 11/2014 |
| WO | 2014182701 A1 | 11/2014 |

OTHER PUBLICATIONS

Coll, Ann R., "Retained Surgical Sponges, Needles and Instruments", The Royal College of Surgeons, 2013, 13 pages.

Gibbs, MD, Verna C, "Therapeutic Packing, Vaginal Packing and Wound Packing: HELP!!! It's All So Confusing", No Thing Left Behind, Slides 1-59, 2013, 62 pages.

International Search Report for Application No. PCT/US2016/029324 dated Jul. 14, 2016, 3 pages.

\* cited by examiner

FIG. 5

| | | | |
|---|---|---|---|
| ID No. RANGE 1 | SURGONS | | |
| ID No. RANGE 2 | NURSES | | |
| ID No. RANGE 3 | SCANNER OPRTRS | | |
| ID No. RANGE 4 | EKG | | |
| ID No. RANGE 5 | ANESTESIA MACHINE | | |
| ID No. RANGE 6 | ROOM LOCATIONS | | |
| ID No. RANGE 7 | SPONGES 10x10 | R | |
| ID No. RANGE 8 | SPONGES 20x20 | R | V |

FIG. 6

INITIAL EVENT ID

FIG. 7

| CURRENT PROCEDURE | |
|---|---|
| ARTICLE 1 | QUANTITY |
| ARTICLE 2 | QUANTITY |
| PREVIOUS PROCEDURE(S) | |
| ARTICLE 1 | QUANTITY |
| ARTICLE 3 | QUANTITY |

FIG. 9

| PATIENT ID |
|---|
| PROCEDURE No. 1 ID |
| PROCEDURE No. 2 ID |

SPONGE COUNTING SYSTEM AND METHOD FOR ENSURING PROPER REMOVAL OF SURGICAL SPONGES FOLLOWING A MEDICAL PROCEDURE

CROSS-REFERENCE TO RELATED APPLICATIONS

This application claims priority to U.S. application Ser. No. 15/569,629, which was filed on Oct. 26, 2017, which claims priority to PCT/US2016/029324 filed on Apr. 26, 2016, which claims priority to Provisional Application No. 62/153,100 filed on Apr. 27, 2015 and Provisional Application No. 62/258,855, filed on Nov. 23, 2015, all of which are hereby incorporated by reference in their entirety.

FIELD OF THE INVENTION

This invention is related to a sponge counting system and method for ensuring proper removal of surgical sponges following a medical procedure, including generating a log of events that occur during the performance of a medical procedure. The log maintained by the system and method of this invention is especially useful for accounting for articles used in the procedure and determining the states of these articles.

FIELD OF THE INVENTION

This invention is related to a sponge counting system and method for ensuring proper removal of surgical sponges following a medical procedure, including generating a log of events that occur during the performance of a medical procedure. The log maintained by the system and method of this invention is especially useful for accounting for articles used in the procedure and determining the states of these articles.

BACKGROUND OF THE INVENTION

It is sometimes useful to maintain a log of the events that occur during an activity. One such type of activity is the performance of a medical or surgical procedure. There are a number of reasons why such a log is useful. It is desirable to account for the whereabouts of articles that are applied to, placed in or used on the patient on which the procedure is performed. These articles include disposable articles such as sponges, towels, suture needles, clips and staples. These articles also include reusable instruments such as forceps and clamps. If one of these articles is inadvertently left in a patient after the procedure is performed, at a minimum it is necessary to perform another procedure to locate and retrieve the article. A further serious consequence of the failure to remove an article from a patient in a timely fashion is that the presence of the article can cause injury or induce an infection. In either case, this adverse result slows the recovery of the patient and increases the cost of patient care. A more serious effect of one of these unintended consequences is that the patient is subjected to permanent harm.

SUMMARY OF THE INVENTION

This invention relates to a new and useful system for maintaining a log of events that occur during the performance of an activity. The system of this invention is especially useful for maintaining a log of activities that occur during the performance of a medical or surgical procedure. Of particular interest, the system can reduce manual entry of data into the log during a surgical procedure, thus optimizing attention of health care professionals on the patient, and improving hospital efficiency.

A further feature of the system and method of this invention is that the log can be used to maintain records or articles used during the procedure. In more preferred versions of the invention, the system and method is further used to produce information that combines data regarding articles used during a prior procedure and data regarding the articles used during a present procedure. Thus the invention is especially useful for maintaining an inventory to determine the status of articles currently used on the patient as well as articles that may have been previously wound packed or implanted in the patient.

Still another feature of this invention is that it provides a means to determine the identity of the HCP generating the log of events. If, during the course of the activity, the HCP maintaining the log changes, the system and method of this invention provides a ready means to identify the substitute HCP who is responsible for maintaining the log.

In terms of hardware, the system and method of this invention includes typically plural portable scanners and a server. The scanners are used to generate event records. There are generally two classes of event records. One type of an event record is a procedure event record. The procedure event record is a record about a specific activity associated with the procedure. Alternatively, a procedure event record can also be a record that contains data describing one of: information that identifies the procedure; personnel performing the procedure; the location of the procedure. The second basic type of event record is an article event record. An article event record contains data describing the relationship of an article relative to the procedure. If the article is a capital item such as anesthesia machine or a blood oxygen monitor, an article record may be made to identify the specific item used in the procedure. The article may alternatively be an article for which there needs to be final accounting at the end of the procedure. These types of articles include non-disposable items such as clamps and implants and disposable items such as sponges. The scanner is used to record article records regarding the states of these articles. For example, when the article is first used on the patient, a scanner generates an article event record that the article is scanned into the procedure. When the article is removed from the patient, the scanner is used to generate an article event record that the article is scanned out of the procedure.

The server stores the event records generated by the plural scanners. These records are selectively downloadable by the scanners.

At the close of the procedure, the scanner is used to determine if there is an appropriate accounting of the scanned in articles. If an investigation reveals that the article is being deliberately left in the patient, the scanner generates an article event record indicating this fact. During a subsequent procedure, the scanner has access to the records that indicate articles were left in the patient. This gives the persons responsible for making the log during the subsequent procedure notice that there needs to be an accounting for both the articles used during this subsequent procedure and articles that were left in the patient during the previous procedure.

BRIEF DESCRIPTION OF THE DRAWINGS

The invention is pointed out with particularity in the claims. The above and further features and benefits of the invention are understood from the following Detailed Description taken in combination with the accompanying drawings in which:

FIG. 5 represents a table of acceptable serial numbers maintained by the system of this invention;

FIG. 6 represents the initial event identification field that is stored by a scanner of this invention when the scanner is initialized;

FIG. 7 depicts the table of unreconciled articles maintained by the scanner;

FIG. 9 is file of procedures for a specific patient;

DETAILED DESCRIPTION

I. Basic System

Figure 1:
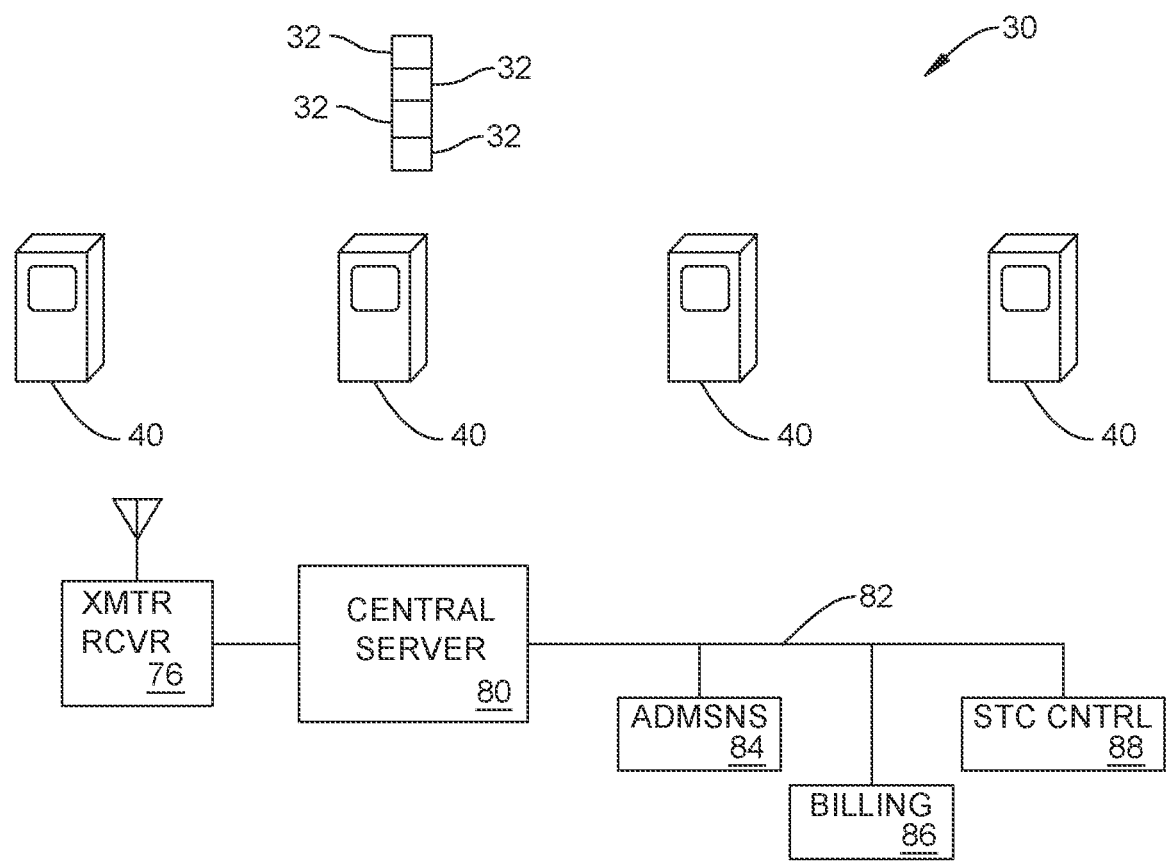
FIG. 1 depicts the basic components of a system for maintaining an inventory according to this invention.

FIG. 1 illustrates the basic components of an inventory control system 30 constructed according to this invention.

The system 30 includes a plurality of HCP event loggers 40. The loggers provide multiple accessible points for data entry. In a medical/surgical facility, these devices 40 are often scanners and are referred to as such throughout this document. Each scanner 40 is used to enter into the system data regarding events that occur during the performance of a medical or surgical procedure. An event that can be logged is that a particular article 32 was used as part of the procedure. In FIG. 1 a set of four articles 32 are shown. System 30 of this invention also includes central server 80. Server 80 maintains records of the articles 32 scanned during the plural inventories system 30 performs. The server 80 is understood to include a processor. The server processor 80 stores the records generated by the system as discussed below. The server processor also responds to the queries sent to the server as discussed below. A wireless transmitter/receiver 76 is shown connected to server 80. Transmitter/receiver 76 facilitates the wireless exchange of data between scanners 40 and the central server 80. Server 80, as discussed below, stores copies of the event records generated by the scanners 40.

Server 80 is connected to other applications run on processors associated with the facility in which system 30 is installed. In FIG. 1, line 82 represents an intranet connection to these applications. It should be understood that these applications may be run on processors external to the facility in which the system 30 is installed. One of these applications is the admissions application 84. Admissions application 84 maintains a patient's electronic medical record (EMR). Application 84 performs this process by, for example, recording data on the admission of the patient to and discharge of the patient from the facility. Server 80 is shown connected to a billing application 86. The billing application 86 generates records of the cost of goods and services associated with the care of the patient. Many facilities have an inventory control application 88. The inventory control application 88 monitors the number of articles available at the facility. The inventory control application 88 provides information to the personnel at the facility regarding the available stock and status of articles available for use in procedures. The inventory control application may also be used to facilitate the automatic reordering of goods when the records indicate the available stock has fallen to a particular level.

It should be understood that each of the above applications as well as the server may all be run from a single processor at the facility where system 30 is installed. It should be understood that the applications may alternatively be run on separate processors. These separate processors may be external to the facility in which the system is installed. It should be appreciated that the server may be wirelessly linked to the scanner 40.

Figure 2:
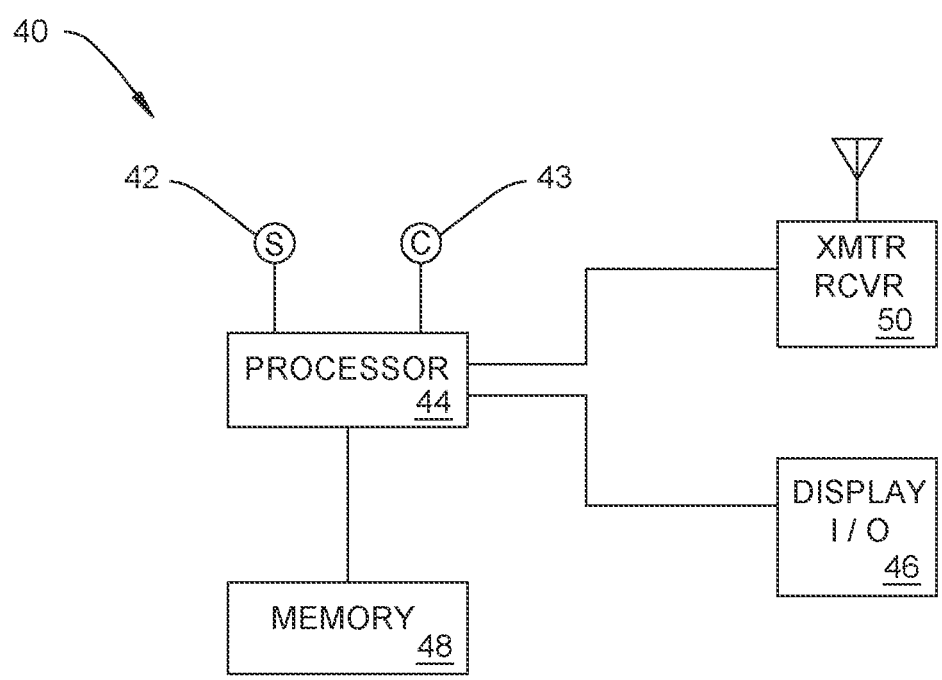
FIG. 2 is a block diagram of the components integral with one of the scanners that is part of the system of this invention.

The basic components of a scanner 40 are now described by reference to FIG. 2. One component of the scanner 40 is scanning head 42. Scanning head 42 reads data from different items placed in proximity to the head 42. The scanning head 42 may take many forms, such as plug-and-play add-on that connects to a mobile device or a tablet. At a minimum, these items include the articles 32 system 30 is employed to inventory. These items may also include items that identify other data associated events in which the article is to be scanned. In a medical/surgical facility these other articles include: a wrist band that identifies the patient on which the procedure is to be performed; an identification card that identifies an HCP associated with the procedure; a code on a work sheet that contains an identification number specific to the procedure; and/or an identification placard that identifies the specific room or location in the facility in which the procedure is to be performed. Physically, scanner 40 may take many forms, such as the tablet or the mobile device that includes scanning functionality.

The scanner 40 records the time that each item is scanned. As one example, the scanner 40 records when the patient is scanned out as the patient leaves an operating room. The scanner 40 sends data regarding this event to the central server 80. The server 80, in turn, sends a notice to housekeeping staff that the operating room is now ready for cleaning so a subsequent procedure can be performed. One or more members of the housekeeping staff can have an identification card or bracelet that is scanned out upon finishing turnover and/or sterilization of the operating room. In response to the same, the system 30 can send a notice to the health care professionals corresponding with the next surgical procedure to be performed in the operating room, with the notice indicating that the operating room is ready for the surgical procedure.

The form of scanning head 42 is not part of the present invention. It should be understood that the scanning head 42 is appropriate to the form of identifying marker integral with the items to be scanned. For example if the identifying markers are bar codes, scanning head 42 is a device capable of optically scanning the bar codes. If the identifying markers are RFID tags, scanning head 42 is an RFID reader.

Some scanners 40 of this invention include a camera head 43. Camera head 43 is a transducer able to generate electronic signals that represent an image of at least a portion of the article being scanned.

The signals generated by the scanning head 42 and camera head 43 are applied to a processor 44 also internal to the scanner 40. The scanner 40 also has user interface sub-assemblies for both manually inputting information and displaying information. In FIG. 2, to avoid redundancy, these user interface sub-assemblies are shown as a single DISPLAY I/O unit 46, such as a tablet. It should be understood that these assemblies may consist of one or more of: a touch screen display; physical buttons; a keyboard; microphone; or an audio output device. The data entered into the input/output unit 46 is applied to the processor 44. Processor 44 also generates the data that is presented on the input/output unit 46. Not shown and not part of the invention are any drivers needed to control the inputting of data to or the outputting of data from the input/output unit 46.

Scanner 40 also includes a memory 48. Memory 48 is where the processor 44 stores information about the events recorded by the scanner 40. Memory 48 also serves as the memory in which the operating instructions for controlling the operation of the scanner 40 are stored. However, memory 48 can serve as the memory in which other instructions can be stored. A transmitter/receiver (transceiver) 50 is also shown as part of the scanner 40. Transmitter/receiver 50 is the unit that wirelessly exchanges signals with the transmitter/receiver 76 to which the central server 80 is connected.

Also, while not shown, it is understood that internal to the scanner is clock. The clock generates data indicating the current time and date, and when each one of the items has been scanned. Scanner 40 also includes a battery, not shown. The battery please the current to the electrically powered components of the scanner 40.

Figure 3:
FIG. 3 depicts the fields in a procedure event record generated and maintained by the system of this invention.

During a procedure, a scanner 40 is employed to generate event records. An event record is a set of data that describes a particular activity or article that is associated with the procedure. Generally, there are two different types of event records. One of the basic types of event records is the procedure event record 102 described by reference to FIG. 3. Generally, a procedure event record 102 contains data regarding an activity associated with a procedure. Here the term data regarding the activity associated with the procedure includes data: identifying the procedure; identifying personnel performing a role in the procedure; identifying the location of the procedure; regarding an activity that occurs during the procedure; and regarding a biological parameter of the patient observed or measured during the procedure.

A procedure event record 102 includes an event identification field 104. Field 104 contains an identifier unique to the record 102. A procedure identification field 106 contains an identifier that identifies the procedure with which the activity is associated. A scanner operator field 108 contains an identifier unique to the HCP operating the scanner 40. Data regarding when the record is created or when the event occurred is entered in a time field 110.

A procedure event record 102 includes an event type field 112. Event type field 112 contains an identifier specific to the activity with which the record 102 is associated. Many procedure event records 102 include one or more subject identification fields 114. Each field 114 stores data that specify the characteristics of the specific activity.

One such activity for which record 102 may be generated is an indication that records are to be generated for a new procedure. In this situation, the event type field 112 contains data indicating that a new procedure is starting. A first one of the subject identification fields 114 holds data that identifies the patient on whom the procedure is to be performed. A second subject identification field 114 stores data that identifies the type of procedure.

A procedure event record 102 may contain data identifying one of the HCPs involved in performing the procedure. In this situation the event type field 112 contains an identifier that indicates the record is being used to record the name of the surgeon; anesthesiologist; scrub nurse; circulating nurse; or other HCP involved in the procedure. The data in the subject identification field 114 identifies the name of this particular HCP. This identifier may be scanned or counted-in from the bracelet or identification card of the HCP.

The identification of the HCPs performing the procedure can be compared to data regarding individual requirements or preferences. These requirements or preferences can be general or uniquely specified for a specific procedure or procedure type. The individual requirements or preferences could be related to any suitable article. Examples of articles or article-related information includes equipment or equipment settings, instrumentation, surgical supplies, patient preparation, patient pre-operative treatment or medication, patient post-operative treatment or medication, surgical or procedural methods, patient position, room temperature or humidity, communication methods, display positions and content, video or photographic images, audio preferences, personal protection equipment or a multitude of other items that could be specified by a HCP performing the procedure. Based on the identification of the HCPs performing the procedure and the known requirements and preferences corresponding with those identified HCPs, the system could make the procedure and the preparation of the procedure more efficient and accurate. For example, the system could compare the articles that have been scanned or counted-in for a procedure to the list of articles required for the same procedure and then indicate when all articles are available or indicate which articles are still required. The system could enable the HCP to use the wireless network to contact another HCP outside the operating room and instruct this HCP to deliver the required articles or other supplies or perform another required action. The system 30 could also communicate with the input/output unit 46, such as the tablet, of the user interface sub-assembly or other portion of the system 30 to ensure that they are set in accordance with the requirements or preferences for the procedure.

A procedure event record 102 may contain data identifying where the procedure is being performed. In this situation, the event type field 112 contains an identifier indicating that the record 102 is being used to record this location information. The subject identification field 114 is where the data identifying this location are stored.

The procedure event record 102 may contain data describing a particular event that occurred during the procedure and a timestamp corresponding with the same. For example, the data may indicate the time the anesthesiologist indicated that the patient was properly anesthetized. Other examples of activities include: opening the surgical site; administering a pharmaceutical; administering a blood transfusion; and closing the surgical site. These events are defined by the times at which they occur. Accordingly, the procedure event record for some of these activities may not include any subject identification fields.

As described above, the procedure event record 102 may include data describing an observed or measured parameter of the patient. If the record 102 includes these data, the event type field 112 contains data that identifies the type of observed parameter. The subject identification field 114 contains the quantifying information associated with the parameter.

The scanner 40 transmits the data of the procedure event records 102 to the central server 80. The central server then transmits these data to the billing application 86 and the admissions application 84. The billings application 86 uses the data to generate or update a bill for the patient, such that the bill includes the costs of activities represented by the data. Moreover, the admissions application 84 uses the data to update the patient's EMR to include information on procedure events represented by the data, the data could also be uploaded into other databases such as national patient registries. Thus, the system 30 includes multiple components communicating with one another to update the patient's EMR, applicable databases and the corresponding bill.

Figure 4:
FIG. 4 depicts the fields in an article event record generated and maintained by the system of this invention.

The second basic type of event record is the article event record 122, depicted with reference to FIG. 4. An article event record 122 contains data that describes the relationship of the article to the procedure. An article 32 may be a capital item that is used during the procedure. Examples of such articles include powered saws and anesthesia machines. An article may be an item that is used during the procedure and then discarded or reprocessed. Examples of these articles 32 include saw blades and burs. An article 32 may also be an implant or a compound that is introduced into the patient. An article event record 122 corresponding with implants contains data that provides the implant's part number, description, and lot number, which can be transferred to the billing application 86 for efficient billing and coding or the data could be uploaded into other databases such as national patient registries. Examples of compounds introduced into the body can include pharmaceutical compounds, bone cement powders, and bone cement monomers. Examples of other articles used during the procedure can include blood and medication, these and other articles can be compared to relevant data in the patient's EMR such as allergies, currently prescribed pharmaceutical compounds, and blood type and provide an alert to prevent an allergic reaction, undesired pharmaceutical compound interaction, or improper blood transfusion. The article 32 may include one or more identifying markers in the manner described above. An article 32 may also be an article that is applied to the patient the presence of which needs to be inventoried and accounted for as the procedure concludes. Non-disposable articles of this species include sterilization trays and their contents, including but not limited to surgical supplies, such as clamps. The article event record 122 corresponding with the surgical tray can include data, such as a unique identifier, a timestamp for the last equipment sterilization, and a load number. This information may be manually input, or may be obtained by using the scanner 40 with the identifying marker associated with the article. Disposable articles of this variety include sponges, towels, suture needles and powered surgical irrigators. The article event record 122 corresponding with disposable articles can include data, such as unique identification information used to reduce the number of retained surgical items.

An article event record 122 includes the previously described event identification field 104, procedure identification field 106, scanner operator field 108 and time field 110.

The article event record 122 includes the previously described event type field 112 for the procedure event record 102. The event type field contains data indicating how an article is associated with a procedure. A sizable percentage of the types of events associated with an article is the scanning in of the article. The "scanning in" of the article is the indication that the article is being used in the procedure. As discussed below there may be other events associated with an article 32.

Instead of a subject identification field, the article event record 122 includes an article identification field 124. The article identification field 124 contains the unique identifier for the article with which the event is associated. An article event record 122 also includes a reconciliation flag field 126. Reconciliation flag field 126 contains a flag that indicates whether or not the article is of the species for which there needs to be an accounting, a reconciliation, as the procedure winds down. The reconciliation flag field is normally empty, the flag is not set. As discussed below, when some articles are scanned into the system, the flag in field 126 is set to indicate that the article needs to be reconciled.

Some article events records 122 include a supplemental data field 128 or an image file 130. The supplemental data includes additional information about the article 32 that is the subject of the record 122. Data that forms an image of the article 32 are stored in the image file 130.

The scanner 40 transmits the data of the article event records 122 to the central server 80, which then transmits the same to the billing application 86 and the admissions application 84. The billing application 86 utilizes the data to generate or update the bill to include the costs of articles used during the surgical procedure and represented by the data of the records 122. The admissions application 84 uses the data to update the patient's EMR and national patient registries, such that they include information on the article events corresponding with the data. Moreover, the central server 80 transmits the data of the record 122 to the inventory control application 88, which uses the same to update the number of related articles available at the facility.

Each scanner 40 does more than generate procedure event records 102 and article event records 122. Each scanner 40 maintains tables of data useful for operating system 30 of this invention. Each of these tables is stored in the memory 48 internal to the scanner 40. One of these tables is a table of acceptable identification numbers, table 140, seen in FIG.

5. As implied by the name, table 140 contains a list of acceptable identification numbers for the personnel, the locations and articles for which the records 102 and 122 may be generated.

In FIG. 5 table 140 is shown as having plural records 142, three records 142 identified. Each record 142 is understood to be associated with a particular range of identification numbers. Table 140 contains more than these data. Associated with each identification number is at least one tag. A first tag identifies the type of person, location or article with which the identification number is associated. In the example of FIG. 5, the identification numbers in a first range of identification numbers are associated with surgeons. The identification numbers in a second range of identification numbers are associate with nurses. The identification numbers in a third range of identification numbers are associated with scanner operators.

The identification numbers within the fourth and fifth ranges of identification numbers are associated with capital items that may be used in a procedure. The example in theses ranges are, respectively, EKG machines and anesthesia machines. The identification numbers associated with the sixth range of identification numbers are the identification numbers associated with the spaces within the facility at which the procedure can be performed.

The seventh and eighth ranges or identification numbers are of articles 32 that may be used during a procedure for which a reconciliation is necessary. In the example of FIG. 5, the ranges of identification numbers are for two different sizes of sponges. Accordingly, within table 140 the records associated with the identification numbers for these articles includes there is a second tag, a reconciliation flag. In FIG. 5, the presence of the letter "R" functions as this flag.

The eighth record also contains a third tag, a virtual identification flag. In FIG. 5, the presence of the letter "V" functions as this flag. The purposes of the reconciliation and virtual identification flags are discussed below. These flags are not always associated with articles. The virtual identification number flag, when present, need not always be accompanied by a reconciliation flag.

Each scanner memory 46 also has a field 143, seen in FIG. 6, in which the scanner stores data representative of an initial event identifier the scanner is supposed to employ. These data are obtained from the server 80 as discussed below. The data in field 143 identify the initial identification number the scanner writes into the event identification field 104 for the first record 102 or 122 the scanner is to generate at the start of a procedure. After this record 102 or 122 is generated, an application running of the processor 44 increments by one the event identifier. This event identifier is then written into the event identification field 104 for the next record 102 or 122 generated by the processor. This process repeats for the subsequent records 102 and 122 generated by the scanner processor 44.

For the procedure, the scanner processor 44 also maintains a table of scanned in articles for which reconciliation is required, table 146, seen in FIG. 7. Table 146, as illustrated, includes two sub tables. A first sub table contains records of reconcilable articles scanned in as part of the procedure. A second sub table may be present. The second sub table, when present, contains records regarding what are known as partially reconciled articles. These are articles associated with the patient in prior procedure for which there needs to be an accounting. Each sub table contains at least one record 147. Each record 147 contains a field that identifies a particular type of article. Each record 147 also contains a field indicating the quantity of the articles.

Figure 8A:
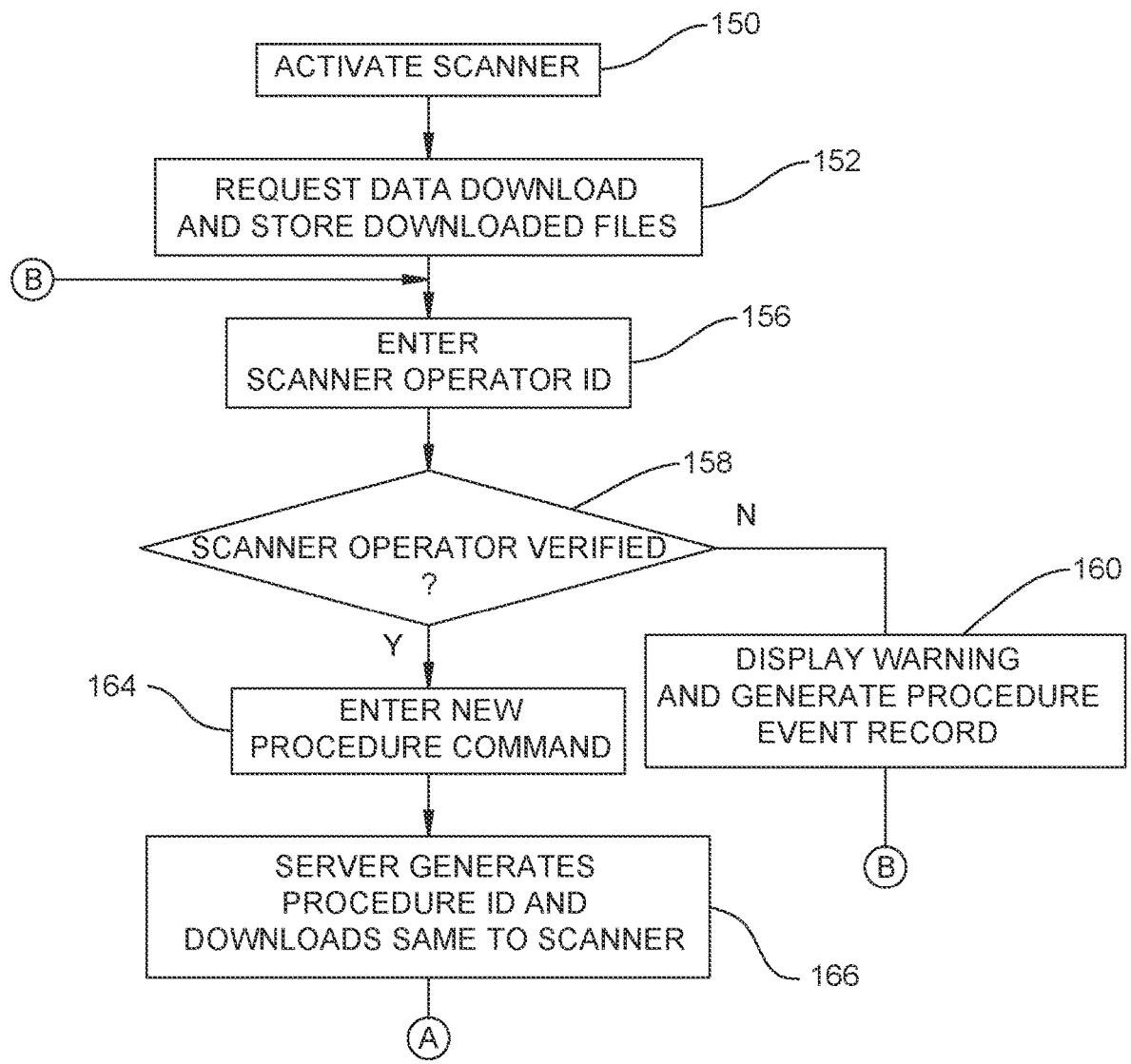
FIGS. 8A and 8B depict the process steps executed when a scanner of this invention is initially prepared for use at the start of a procedure.
Figure 8B:
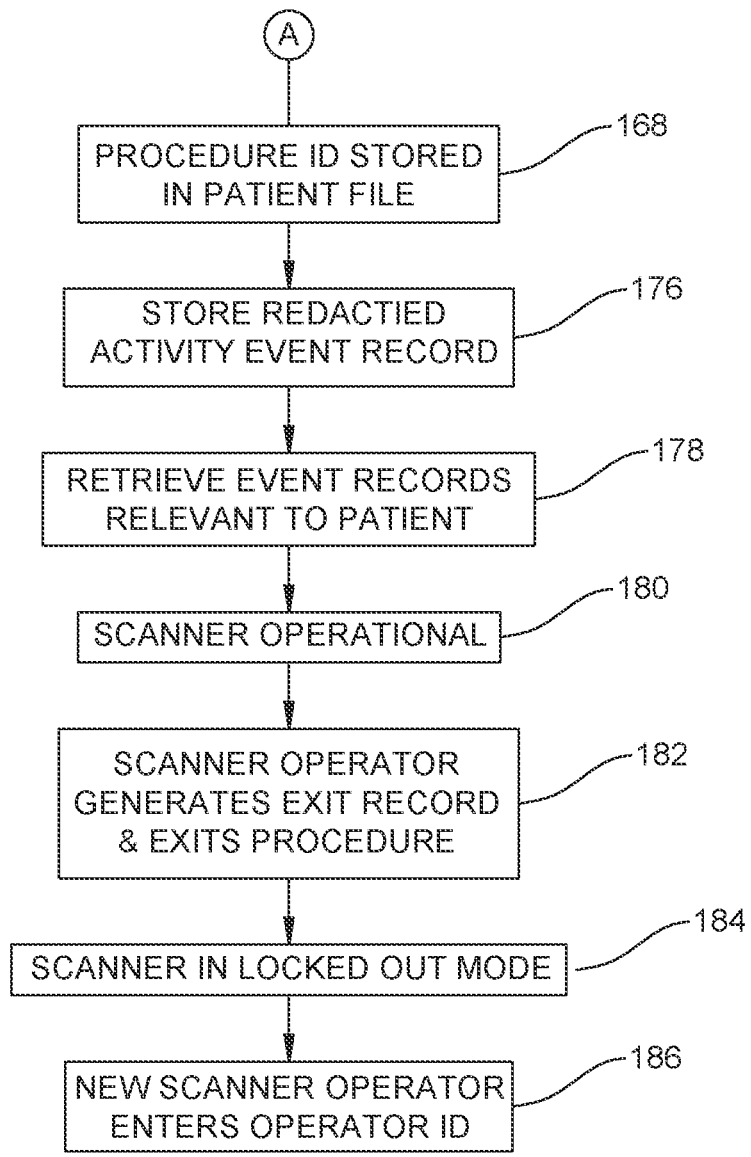

FIGS. 8A and 8B illustrate the process steps typically executed when a scanner 40 is initially turned on. Scanner 40 is usually turned on prior to the start of the procedure. Step 150 is the actual turning on, activation of, the scanner 40. As part of step 150 scanner performs any necessary self checks, the execution of which is not part of the present invention. After the self checks are performed, the scanner 40 queries the central server 80 to ensure that the scanner has the most recent copies of the files and tables stored in the scanner, step 152. These files and tables include the table of acceptable identification numbers 140 and the initial event identifier for storage in field 143. Additional files that are scored in the scanner that may need updating include the below discussed file that lists article that are not to be used. As part of step 152, if it is determined that the scanner 40 does not have the most current tables or files, the most current versions of these data are downloaded to the scanner.

At this time, the scanner 40 is not ready for use. To make the scanner ready for use, the operator enters the operator identification data unique to this individual, step 156. In an initial sub step of step 156, the scanner processor 44 presents a message on the display I/O unit requesting that these data be entered. Different means can be used to enter these data. For example, these data can be entered by scanning a bar code imprinted on the individual's name badge. The individual may enter these data by manually entering and identifying code into the scanner display I/O unit 46. Scanner processor 44 then compares the entered data to the data in the table of acceptable identification numbers 140, step 158. More particularly, in step 158, the scanner processor verifies that the entered identification number corresponds to the identification number of an individual authorized to operate the scanner 40.

If the evaluation tests negative, scanner processor 44 generates a warning, step 160. In some versions of the invention as part of step 160, the scanner processor may generate a procedure event record 102 and download the record to the server 80. This record 106 is generated prior to complete initialization of the scanner 40. Therefore a procedure identifier has not been assigned to the procedure. This record 102 therefore does not include data in the procedure identification field 106. The scanner operator field 108 contains data indicating the identification number that was scanned into the scanner 40. The time field contains data, based on the clock internal to the scanner, indicating when this event occurred. The event type field contains a code indicating that an unauthorized individual attempted to log in as the scanner operator. The loop from step 160 to step 156 is meant to represent that the scanner processor 44 waits for an authorized individual to log into the scanner 40.

Most likely, the individual logging in to use the scanner 40 is the individual authorized to use the scanner. The evaluation of step 158 tests positive. When this event occurs, the individual enters data into the scanner to indicate that a new procedure is to begin, step 164. As part of the entry of these data, the scanner operator enters both the name of the patient and the type of procedure. The name of the patient may be obtained by scanning a wrist band attached to the patient. The type of procedure may be entered through the display I/O unit 46. The procedure data may be entered by highlighting a specific procedure from a list of procedures on a menu presented on the display I/O unit. Once these data are entered, at the conclusion of step 164 these data are sent to the server as part of a procedure event record. The event type field 112 for this record 102 indicates that the type of the event is the start of a new procedure. The procedure identification field is blank. For this and all subsequent records 102 and 122 created by the scanner 40, the scanner processor places the identifier for the logged in scanner operator in the scanner operator field 108. One subject identification field 114 contains data that identifies the patient. A second subject identification field 114 contains data that identifies the type of procedure.

In response to this event record, the server 80 performs a number of functions. One of these functions, step 166, is the generation of a procedure identification number unique to this procedure. As part of step 166, this identification number is downloaded to the scanner. Also in step 166 this identification number is placed in the procedure identification field of procedure event record 102 uploaded from the scanner 40.

The procedure identification number is also stored in a patient procedure file 170 now described by reference to FIG. 9. The patient procedure file 170 contains a first field, a patient identifier field 172. Field 172 is the record that identifies the patient with particularity. File 170 contains one or more procedure identification fields 174. Each field 174 contains the identifier for a specific one of the procedures to which the patient was subjected. Thus in step 168 the procedure identifier stored in the previous step 166 is stored in the procedure file 170 for the appropriate patient.

In step 176 the procedure event record 102 is stored in the server database of procedure event records 102 and article event records 122. The record stored is a partially redacted procedure event record. Specifically, the patient-specific identifying data, the data in the first subject identification field 114, is removed. Thus, it is a feature of this invention that the database of procedure event records 102 and article event records 122 do not contain data that specifically identify the patients with which the event is associated. To obtain this information, it would be necessary to query the file that contains the plural patient files 170. It is an assumed feature of this invention that only designated individuals are able to access files 170.

In step 178 the server 80 determines if there are any event records relevant to the patient that need to be downloaded to the scanner. If this evaluation tests positive, these records are downloaded to the scanner 40 for storage in the scanner memory 48. The reason these records may exist is discussed below.

At this time, the scanner 40 is ready for use to record events associated with the procedure. In FIG. 8B, this is called out as scanner operational step 180. The use of the scanner is discussed below. It should be appreciated that each time a procedure event record 102 or an article event record 122 is created, the procedure identifier for the article received from the server 80 is written into the field 106. The data indicating the scanner operator is entered into the field 108. The process of creating records 102 and 122 is discussed with respect to FIG. 10A-10D.

Steps 182-186 represent what occurs if, during the course of a procedure, a new individual assumes the role of scanner operator. This event can occur because shift change or a determination that the current scanner operator is required elsewhere. If a switch is necessary, the current scanner operator, in step 182, enters into the scanner an activity event that he/she is logging out as the scanner operator. As part of step 182 the scanner generates a procedure event record 102. This particular procedure event record contains event type data that the scanner operator has logged out of the current procedure.

As represented by step 184, scanner 40 then enters a locked out mode. When in the locked out mode, scanner 40 cannot be used for generating records 102 and 122. The scanner remains in the locked out mode until in step 186 a new individual logs in as the scanner operator. Step 186 it is understood is combination of the previously described steps 156, 158 and 160. If it is necessary to execute step 160 the procedure event record 102 that is generated contains in field 106 data identifying the procedure in which the unauthorized individual attempted to log in as the scanner operator. Most likely though in step 158 the evaluation will indicate that the person logging in is authorized to operate the scanner. The scanner returns to a state in which the scanner is able to generate records 102 and 122. Even when it is determined that an authorized person is now using the scanner 40, as part of step 186, the scanner processor 44 generates a procedure event record that documents this event.

FIGS. 10A-10D depict steps that are executed when a scanner 40 is used to either log the state of an activity, log the state of an article 32 or determine the history of an article as part of system 30 of this invention. A first step, step 202, includes using the scanner to record whether the event corresponds with a procedure or an article. Generally, a scanner 40 is used to log a procedure event or an event associated with an article. For the purposes of understanding this invention, the event logging by the scanner is further understood to mean the use of the scanner to determine the history of the article. The entry of the scan type is performed by the scanner operator depressing a button presented on the display I/O 46.

Step 204 is the determination by the scanner processor 44 that the operator wants to generate a procedure event record 102. Processor 44 makes this determination if, in step 202, the scanner operator indicated that this is the type of event to be logged. Once processor 44 makes this determination, the scanner operator, in step 206, enters into the scanner 40 an indication of the type of activity to be logged. As part of step 206 it is understood that the processor 44 presents on the display I/O a menu or other visual images that invite the operator to enter data indicating the nature of the event to be logged. The event may be the recording of the identity of an individual participating in the procedure. The event may be the recording of the location of the procedure. The event may be an actual activity that occurs during the procedure. These activities include: a timestamp or indication of when the patient is brought into the operating room; an indication of when the patient is fully sedated; an indication of when a particular step of the procedure being performed on the patient starts or is completed.

Step 208 is the entry of the specific identifier associated with the procedure event. These data entry may be entered by using the scanner 40, in particular the scanning head 42, to read a marker associated with the event. For example, if the event concerns the logging in or logging out of an individual, the identity of the individual may be obtained by the scanning of a bar code on the individual's identification badge or wristband. If the event is the logging of the location of the procedure, the identification process may involve scanning a bar code on a placard in the room.

Alternatively, the identifier may be entered by depressing buttons presented on the scanner display I/O unit 46. Typical event identifiers are entered through the display I/O unit when the event to be logged is an activity associated with the procedure. These activities include the identification of the type of the procedure or an indication that a particular step of the procedure has started or is completed.

After step 208 is executed the processor, in step 210, compares the entered identification data to the list of acceptable identification data in table 140. Step 210 is similar to the previously described steps 158 and 160. If the comparison tests negative a warning similar to that of the warning of step 160 is generated. As part of the generation of the warning, a procedure event record 102 may be generated. This record contains data indicating the person performing the scanning and the procedure with which the event is associated. The event type field indicates the event that occurred was the unsuccessful entry or an incorrect identification number into the system 30. To minimize redundancy in this document, the execution of these steps is not further illustrated in the flow charts. Further, it should be understood that these steps can occur whenever scanner processor 44 determines that unacceptable identification data are entered.

Most likely, the evaluation of step 210 tests positive. The scanner operator is then able to execute another optional step, step 212. Step 212 is the entering of data indicating the time the event occurred. This is because the actual event may have occurred a number of minutes before the process for creating the procedure event record 102. More, often, the time associated with the event is automatically recorded based on the time maintained by the clock in the scanner 40.

Once all the data necessary to log the procedure event are created, the procedure event record 102 is created, step 216. In step 216 scanner processor 44 generates the data for the event identification field based on the data stored in the memory indicating the next ordinal number for the event records 102 and 122. The procedure identifier is stored in field 106. The previously entered identity of the scanner operator is stored in field 108. The time the record is created is stored in field 110. Data based on the event type as defined in step 206 are stored in field 112. The particulars associated with the event, if there are any, are stored in the one or subject identification fields 114. These particulars can include, the data identifying particular individual or the actual time the specific event occurred.

As part of step 216, the procedure event record 102 is stored in the processor memory 56. Also as part of step 216 the event record is also transmitted to the central server 80. Again, as part of step 216, server 80 stores the event record in a file of the event records that are received from the plural scanners 40 that are part of system 30. Scanner 40 is then ready to record a new procedure event record 102 or a new article event record 122, (loop back to step 202 not shown.)

In step 202 the scanner operator may enter an instruction indicating that the scanner 40 is to be used to generate a new article event record 122. There are two basic types of article event records 122 scanner 40 typically generates. Many of the article event records the scanner 40 generates are records indicating that the article is being scanned into the procedure. Here "scanned in" to the procedure is understood to mean that the article is being used as part of the procedure. There are some articles 32 that, during the procedure, are placed in the patient. It is important that at the conclusion of the procedure these articles are not unintentionally left in the patient. Therefore, as the procedure winds down, there needs to be an accounting or reconciliation of these articles. The act of satisfactorily determining the status of an article at the end of the procedure is an event considered the "scanning out" of the article from the procedure. Thus, in step 202 the scanner operator can enter an instruction into the scanner 40 that the scanner is being used to generate an article event record 122 indicating that the article has been scanned out. An article that has been scanned out of a procedure is considered to be an article for which there has been a satisfactory finally accounting, a full reconciliation. In step 202, the scanner operator can do more than indicate the article is being scan in to the procedure. Alternatively, the scanner operator can enter an instruction indicating that the article should be considered to be scanned out of the procedure.

Step 222 is the recognition by the scanner processor 44 that the scanner 40 is to create a record indicating that the article has been scanned into or scanned out of the procedure. Step 224 is the scanning of the marker associated with the article. Alternatively, if the marker is not readable, or there is no marker, in step 224, the identifying number associated with the article is manually entered into the scanner display I/O unit 46. After the article identification number is entered into the scanner 40 the identification number is compared to the list of expected identification numbers, step 226. There are actually two versions of step 226. If the article 32 is being scanned into the procedure, in step 226 the entered identification number is compared to the identification numbers in the table of acceptable identification numbers 140. If the article 32 is being scanned out of the procedure, in step 226 the identification number is compared to the identification numbers of the article event records 122 stored in the scanner for articles scanned in during the procedure for which reconciliation is required.

Not shown are the warning displayed and article event record 122 that are generated if the evaluation of step 226 indicates that unusual event occurred. During the generation of a record 122 documenting the scanning in of the article, the unusual event is a determination that the identification number for the article is not contained in the table of acceptable identification numbers 140. During the generation of a record 122 documenting the scanning out of an article, the unusual event is a determination in step 226 that the article was never scanned in. In other words that there is no predecessor record indicating that the article was previously associated with the patient.

Step 228 is an optional step of entering supplemental data about the article. For example, when an article is scanned out, these data can indicate that: the articles was applied to the patient; or the article was prepared for use but not actually applied to the patient.

Another supplemental step that may be executed is the recording of an image of the article, step 230. More often than not, there is no requirement to record an image of an article. However, there are situations when such an image is necessary. For example when generating a record 122 regarding the scanning in of article, the article may be one that owing to its design, it is not practical to attach an identifying marker. More often, an image is stored when creating a record 122 of the scanning out of an article. This is because, owing to the use of the article, the marker is either fractured or so covered with fluid and semi-solids that the article is not readable.

Regardless of the reason, when it is necessary to record an image of an article, camera head 43 is used to record the image.

In some constructions of the invention, there may be a set of conditions in which the scanner processor 44 requires the execution of step 230, the recording of the article image. For example, as discussed above, there may be instances where during the scanning out of the article the scanning head 42 is not able to read the machine readable marker. If this event occurs, processor 44 may require an image of the article to be captured to complete the scanning out of the article. The image will be part of the article event record 122. The image thus becomes part of the file so as to provide recorded visual proof that the article was subjected to a reconciliation.

Once the data required for the article event record are generated, in step 236, scanner processor 44 creates the article event record 122 for the article 32. The data for fields 104, 106, 108 and 110 are filled the same way these data are filled in when a procedure event record 102 is generated. Based on the indication in step 202 that the event is the scanning in or scanning out of an article the appropriate event type data are stored in field 124. The identification number for the article is written to the article identification field 124.

In step 236 the reconciliation flag 126 of the article event record 122 may be set. Normally this flag is off. This means that the article with which the record is associated is not an article the presence of which needs to be reconciled at the end of the procedure. As part of the process of creating the article event record 122, the scanner processor reviews the record 142 associated with the identification number for the article in table 140. If this record indicates that the reconciliation flag is set for the article, in step 236, the processor 44 sets the flag 126 in the record to indicate the article is to be reconciled.

If supplemental data are present for the article 32, these data are written to the supplemental data field 128 for the article. If an image of the article was made, the image is stored in the image file field 130.

Also as part of step 236, the article event record is stored in two locations. First the record 122 is stored in the local memory 46 internal to the scanner 40. A copy of the article event record 122 is transmitted to the central server and stored in the server's file of facility event records 102 and 122.

As a result of the scanning of the article 32 it may also be necessary perform a step 238 and update table 146, the table of reconcilable articles. One event which requires the execution of step 238 is the scanning in of an article that requires reconciliation. If this event occurs, the processor 44 based on reference to table 140 first determines if a record 147 has been generated in the table 146 for the specific type of article. For example if the article to be reconciled is a 20 cm×20 cm sponge, processor 44 determines whether or not table 146 includes a record 147 for this type of sponge. If the evaluation tests negative, the record 147 is created and the quantity field is populated with a value of one. If the evaluation tests positive, for the particular type of article, the count in quantity field is incremented by one.

Another event which results in the execution of step 238 is the scanning out of a reconcilable article. If this event occurs, the count in the quantity field of record 147 associated with the type of article is decremented by one.

Alternatively, an article may be scanned to determine the status of the article. This event can occur if, during a time period in which an operating room is being cleaned an article that appears it should have been the subject of reconciliation process is found on the floor. When it is necessary to so determine the status of an article, in step 202 the scanner operator enters an instruction indicating that the history of an article to be scanned is requested. For the ease of understanding the system 30 of this invention, it will be assumed that if the evaluations of steps 204 and 222 both test negative, processor 44 recognizes that the instruction entered into the scanner was an article history request. Step 248 represents the scanning of the article marker or the manual entering of data containing the identification number for the article.

Once the identification number is entered, in step 250, the history of the article is retrieved. More particularly in step 250, the scanner 40 sends a request to the server for all the article event records 122 associated with the article 32. It should be understood that this request includes the identification data for the article. In response to this request, as part of step 250, the server 80 retrieves from its files the event records all the records 122 related to these articles. The records are transmitted to the scanner 40. Step 252 represents the display of the information contained in these records on the scanner display I/O unit 46.

Step 254 represents the evaluation of whether or not it is appropriate to generate a new article event record 122 of the article. Generally, two variables determine whether or not the generation of such a review is necessary. One factor is the history of the article. A second factor is the circumstances leading to the query about the history of the article. As a result of review of the article event records it may be determined that the article is currently in a relatively innocuous state. This condition may exist if it is determined that the event type field 112 for the last record 122 indicates that the last known state of the article was the scanned out state. If this is the current state of the article, an acceptable protocol may be the simple final disposal of the article without any additional event logging.

Alternatively, the history of events associated with the article may indicate that there is a need to generate a new article event record for the article. This condition may exist if it appears the article was scanned in but never scanned out. Alternatively, this condition may exist if the article was previously classified as being in a partially reconciled state when, in fact, the article was located on the floor of the facility.

If, in step 254 it is determined that a new record 122 is appropriate, the record is generated in step 260. Step 260 is similar to previously described step 236. When this article event record 122 is generated, the procedure identification field 106 may be filed with data indicating the record is being generated as part of a housekeeping or an inventory procedure. The scanner operator in step 260 may also enter into the scanner indicating how the article is to be classified. One such state may be the previously described scanned out state. Another state may be a state indicating that the article was subject to a disposal process. The scanner operator may enter data indicating that the article is in this state if a review of the article history indicates that there were never any previous records 122 for the article. Once information indicating the designated state for the article are entered, scanner processor 44 writes this information into the article event record in field 112 as the event type information for the article. As part of step 260, this new article event record 122 is uploaded to the server 80 and stored in the procedure and article event file.

Figure 10A:
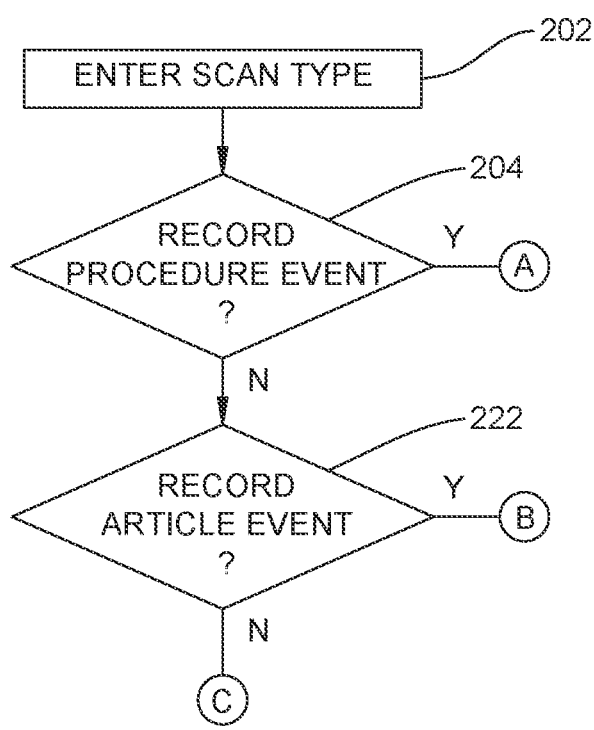
FIG. 10A-10D form a flow chart of the process steps executed when the system of this invention is employed to generate a procedure event record, an article event record or determine the history of an article.
Figure 10B:
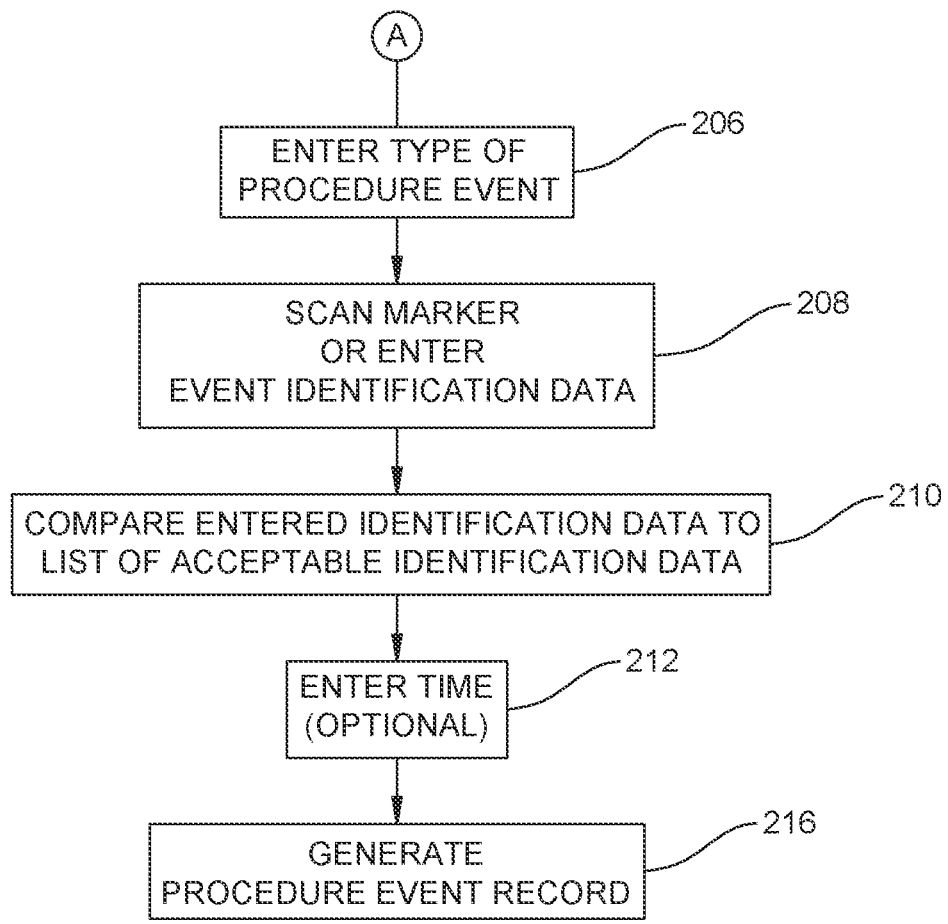
Figure 10C:
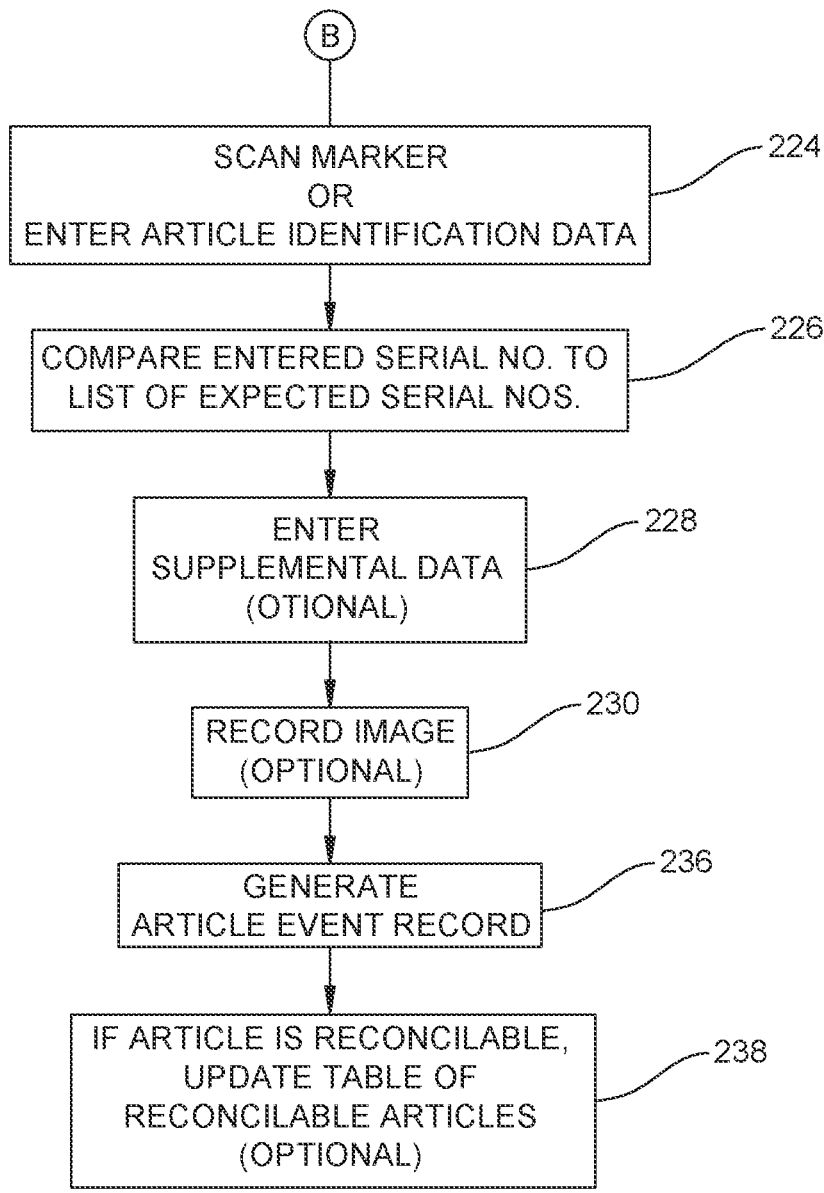
Figure 10D:
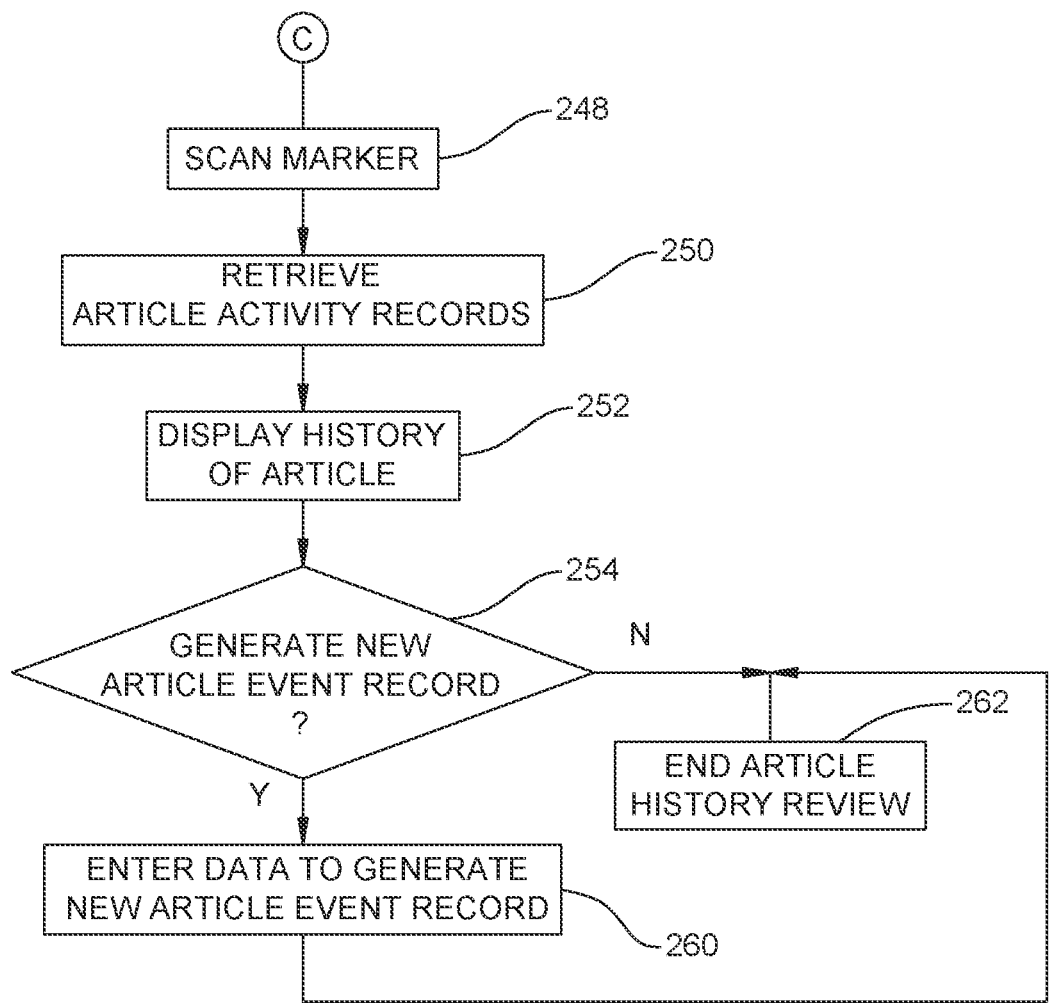

Step 262 in FIG. 10D represents the end of the article history review process. This process can be considered concluded if it is determined in step 254 that there is no need to generate a new article event record. The process alternatively concludes with the generation of the new article event record in step 260. Not shown is the loop back from step 262 to step 202.

Figure 11:
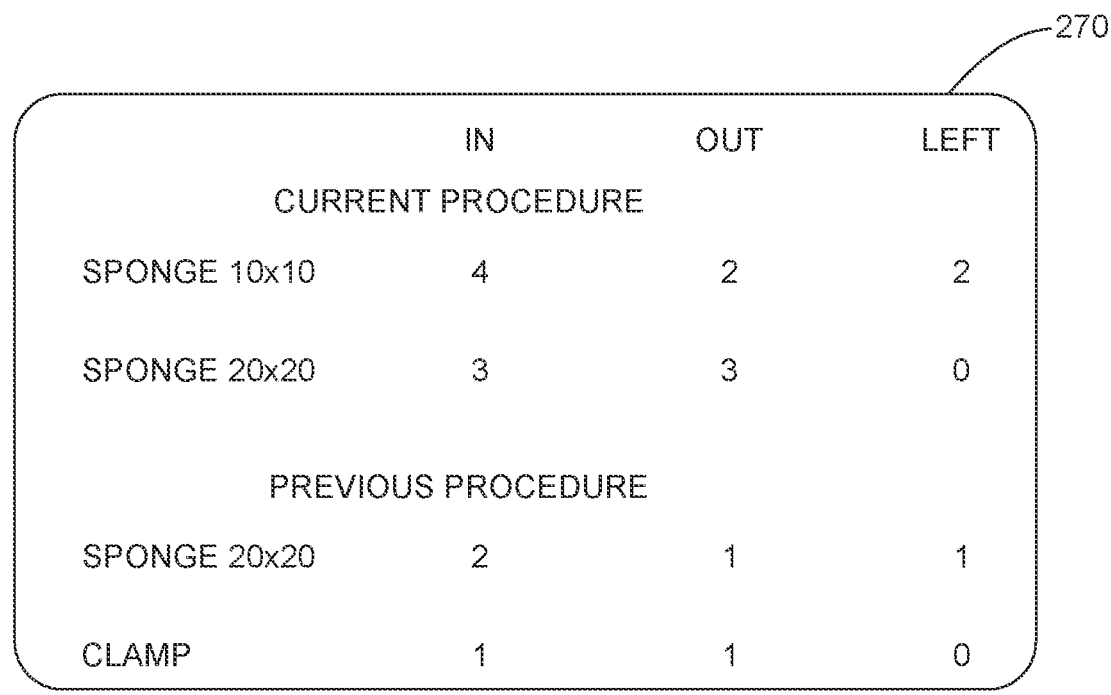
FIG. 11 represents how data regarding articles that need to be reconciled are presented on the scanner display I/O unit.

During the course of the procedure it is desirable to determine the number of articles scanned into the system for which reconciliation is required. By entering an appropriate command on the display I/O unit an image 270, seen in FIG. 11, is presented on the display I/O unit of the articles 32 for which reconciliation is required. (Not shown are the process steps that result in the generation of the image 270.) For each type of article there is a row of information. This information includes: text identifying the type of article; the number of articles scanned in as part of the procedure; the number of articles scanned out; and the number of articles that appear to still be remaining in, left in, the patient. The most critical of these data are the data indicating the number of articles left in the patient. This is why the image of this number may be presented in highlighted color. Color not depicted in FIG. 11.

In some versions of the invention if all of one type of article has been counted out, text in the row associated with that article type is displayed in green. If some of the articles of that type have not yet been scanned out, text in the row associated with that article type is displayed in red. If articles were wound packed in previous procedures, text in the row associated with that article is displayed in orange. This color coding of article information more communicates the current status of the various articles to the scanner operator. This color coding of article information is also used in other images presented by the scanner display, such as when an article's history is displayed in step 252 of FIG. 10D.

In image 270 the articles for which reconciliation is required are further divided into two categories. The first category are the articles scanned in as part of the current procedure. The second category, if it exists, are for articles scanned in during a prior procedure.

Scanner processor 44 generates the data presented on image 270 based on the data in the article event files 122 for the procedure. Based on the records of scanned in articles, the processor 44 determines the number of each type of scanned in article for which reconciliation is required and the number of those articles that have been scanned out. The difference between these two quantities yields the number of articles for which reconciliation is required. In regard to articles scanned in from the previous procedure, the initial number comes from the below discussed table of partially reconciled articles, table 308.

Figure 12:
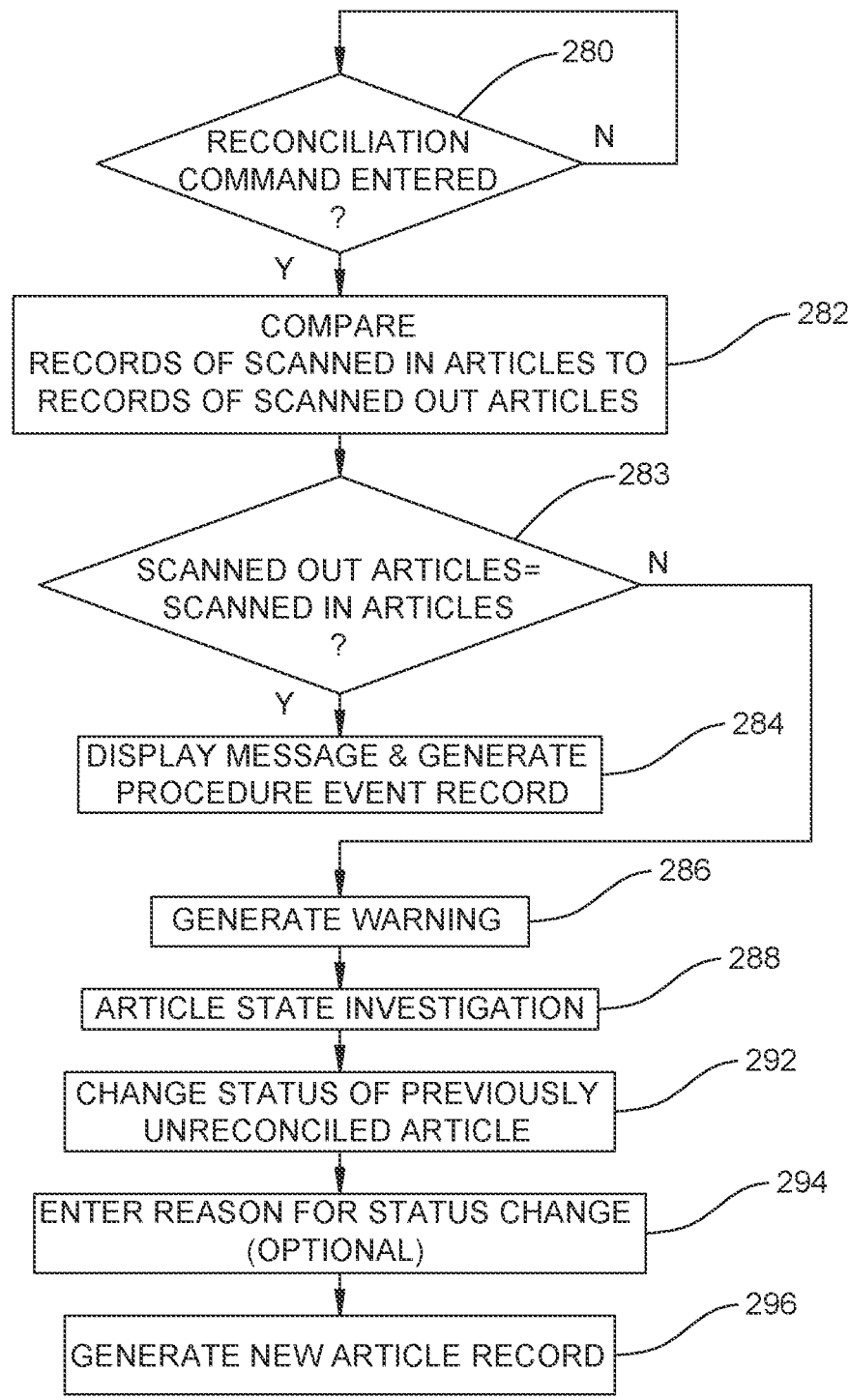
FIG. 12 is a flow chart of the steps executed to reconcile articles used during a procedure.

As the procedure winds down, it may be necessary to perform a final accounting of the articles 32 for which a reconciliation is required. System 30 assists in performing this reconciliation. Specifically, step 280 of FIG. 12 represents the entry of a command into the scanner 40 that a reconciliation of the articles is required. In response to the entry of this command, in step 282 the processor determines whether or not all the reconciled articles scanned into for the procedure have been scanned out. This evaluation may be performed by comparing for each reconcilable article for which there is a record 122 indicating the articles was scanned in, there is also an also a record 122 that the article was scanned out. Step 283 represents the analysis of the results of the comparison of step 282.

If the evaluation of step 283 tests positive, in step 284 a message indicating that the reconciliation was complete is presented on the scanner display I/O unit 46. Also in step 284 scanner processor 44 causes a procedure event record 102 to be generated to indicate a successful article reconciliation. For a single procedure, the completion of the article reconciliation is for the purposes of this invention the last task for which the scanner 40 used in regard to the inventorying of articles.

If the evaluation of step 283 tests negative, scanner processor, in step 286, presents a warning on the display I/O unit 46. This warning may identify with specificity the types of articles for which a reconciliation is required. The articles for which there has not yet been a proper accounting are considered to be unreconciled.

Step 288 represents the investigation that is performed by the individual/individuals responsible for the reconciliation to determine the status/statuses of the article/articles requiring investigation. As a result of this investigation, the articles may be located. This would result in an execution of the steps 202 and 222-238, to scan out previously missing article/articles located as a result of the investigation. If all the articles are reconciled, a subsequent re-execution of steps 280, 282 and 283 will result in an indication that the reconciliation is complete. Not shown is the branching from step 288 to steps 202 and 222-238 when an article that appears unreconciled is located. Also not shown is the link from step 238 to step 280 when, after all unreconciled articles are located, the reconciliation command is again entered.

There may be one or more articles that are neither unreconciled nor fully reconciled. For example, during one surgical procedure some inventoried articles may be deliberately left in the patient. These articles are left in the patient for specific therapeutic purposes. These articles are left in the patient with the understanding that in a second or later procedure the articles will be removed from the patient. For example, when a patient is initially treated after a trauma, some sponges or clamps may be left inside the patient to minimize internal bleeding. The wound is then closed to give the patient's condition time to stabilize before being subjected to additional surgery. This process of leaving articles in a patient is sometimes referred to as wound packing. After the patient's condition is stable, the patient may be subjected to one or more additional surgical procedures. During the second or later procedure(s), the sponges and clamps initially placed in the patient are removed.

System 30 of this invention allows for the inventorying of these articles that, by virtue of being left in the patient, are not fully reconciled. Specifically, if during the procedure wind down, it is determined that the apparently unreconciled articles are intentionally still in the patient, the inventory manager, in step 292, enters an instruction to scanner 40 to change the status of the article 32. For example, if it is determined that the article was intentionally left in the patient, the processor is instructed to generate an article activity record to indicate the article should be considered partially reconciled. Step 294 represents the entry into the scanner of data explaining why it is appropriate to change the status of the article 32. Step 296 represents the generation of the new article event record based on the instructions and information provided in steps 292 and 294. When this particular article event record 122 is generated, the scanner processor enters into the event type field data indicating that the article should now be considered to be in a partially reconciled state. As with the other records 102 and 122, this record 122 is both temporarily stored in the scanner memory 48 and uploaded into and stored in the central server 80.

There are other reasons why it may be appropriate to change the state of an article from scanned in and unreconciled to another state. For example, owing to time constraints or the patient expiring it may be appropriate to terminate reconciliation. In situations such as this, the scanner operator, in step 292, enters an instruction that the status of the article should be changed from scanned in and unreconciled to suspended. Alternatively, after investigation it may be determined that while the article cannot be located it is extremely unlikely that the article was left in the patient. In this situation, it may be decided that the article is most likely deep within a pile of waste and that little would be gained to locate the article. In a situation like this, it may be appropriate to enter an instruction indicating that the status of the article should be changed from "counted in and unreconciled" to "cleared."

From the above it should be appreciated that once it is decided to change the status of an article, steps 292, 294 and 296 are executed to generate an article event record 122 that both indicates the current status of the article and the reason the article is considered to be in that status.

Once the status of the previously unreconciled articles are updated, steps 280-282 are re-executed. It should therefore be understood that in the evaluation of steps 282 and 283 the scanned in articles are not just compared to the scanned out articles. The scanned in articles are further checked against the articles for which the records 122 indicate are in a satisfactory state other than the scanned out state.

Once the investigation of the unreconciled articles is completed and the statuses of these articles is known, the evaluation of step 283 tests true. Accordingly once steps 288-292, 294 and 296 are completed, after the subsequent execution of steps 280 and 282 are completed, the scanner 40 should execute step 284.

Figure 13:
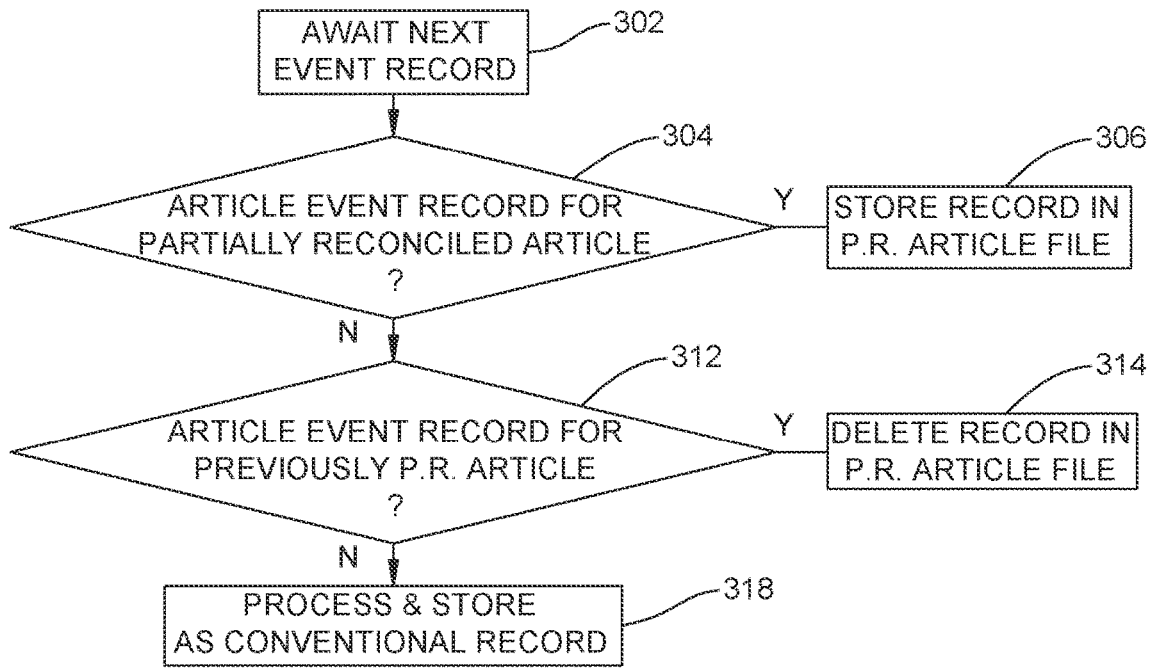
FIG. 13 is a flow chart of how the file of partially reconciled articles is updated.

FIG. 13 represents what happens when server 80 receives an article event record 122 that indicates the status of an article has been changed to partially reconciled. Step 302 represent the server 80 receiving one an event records 102 or 122 that was generated in one of steps 216 or 236, respectively. Step 304 represents the server 80 determining if the received record 122 is a record indicating that an article 32 should now be considered partially reconciled.

Figure 14:
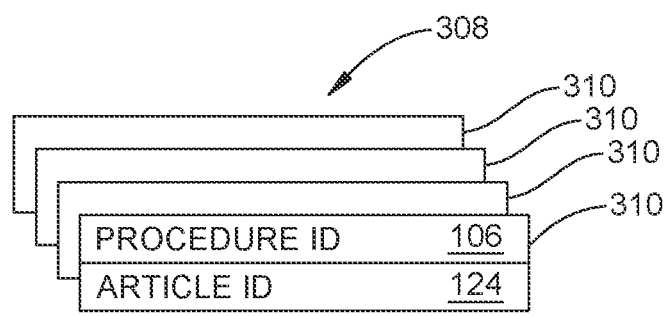
FIG. 14 depicts the file of truncated article event records for articles classified as partially reconciled.

When the evaluation of step 304 tests true, the server 80, in step 306, stores a copy of that article event record 122 in a file of partially reconciled articles, file 308 of FIG. 14. As implied by its name, file 308 contains copies of the subset of article event records for articles that are classified as partially reconciled articles. Each record 310 in file 308 contains data from the article event record 122 that is stored in the main database of event records 102 and 122 maintained by the sever. To minimize space, each record 310 at a minimum may only contain the procedure identifier and the article identifier for the article 32.

Figure 15:
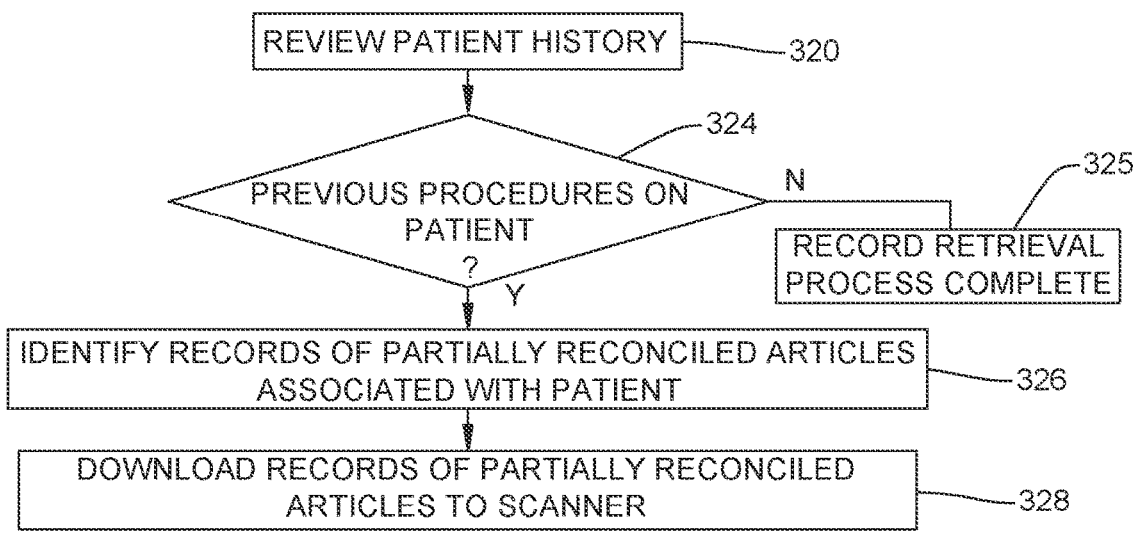
FIG. 15 is a flow chart of how records specific to a patient are identified and downloaded to the scanner used to generate event records about the patient.

The means by which system 30 uses the records in file 308 to facilitate the inventorying of partially reconciled articles is understood by first returning to step 178 of FIG. 8B. FIG. 15 is an expansion of subs-steps performed in step 178 as step 178 applies to records associated with partially reconciled articles. In the initial sub-steps, steps 320 and 324 the processor integral with the server reviewing the patient procedure file 170 to determine if there are records identifying past procedures performed on the patient. For the purposes of retrieving records regarding partially reconciled articles, when the evaluation of step 324 tests negative, the execution of step 178 is considered completed, step 325. The scanner 40 is now essential operation; the scanner advances to step 180 of FIG. 8b.

If the evaluation of step 324 tests positive, the server retrieves the procedure identification numbers for these procedures, step not shown. The server then reviews the partially reconciled articles file 308 in step 326. Specifically, file 308 is reviewed to determine if there are article event records for partially reconciled articles that are associated with the procedures previously performed on the patient. If this review develops such records, copies of the article event records 310 for these partially reconciled are downloaded into the scanner memory 46, step 328. These records 122 are then stored with the other records 102 and 122 stored in the scanner memory 46. The quantities of the different types of these articles are stored as records 147 in table 146, the table of reconciled articles. The storage of these records 122 in the scanner memory can be considered the completion of step 178. Not shown is advancement of the scanner to step 180.

In FIG. 7, table 146 is shown as not having any ARTICLE3 records associated with current procedure. This is because there are new unreconciled ARTICLE3-Type articles associated with the procedure. The only ARTICLE3-Type articles are partially reconciled articles associated with the patient. Similarly, in table 146 there is no ARTICLE2-Type record 147 associated with the previous procedures. This is because, for this particular patient, the only ARTRICLE2-Type articles for which reconciliation are required are articles that were introduced during the current procedure.

During the actual procedure, scanner 40 generates procedure event records 102 and article event records 122 as described with respect to the flow chart of FIGS. 10A-10D. Returning to FIG. 11, it can be seen that image 270 has two categories for article that are subjected to reconciliation inventory. The first category is for the articles scanned in during the current procedure. In the example of FIG. 11, these are the articles listed in the first two rows of the image. Should the data indicate that there are partially reconciled articles associated with the patient, data regarding these articles are displayed as a second category of articles, the articles from previous procedures for which reconciliation is required. This provides the operating room personnel notice that, in addition to needing to reconcile articles from the current procedure, it will also be necessary to reconcile articles from one or more previous procedures. This notice serves as the cue to the medical personnel that during the procedure, typically before the incision into the patient is closed, there should be an investigation to retrieve these partially reconciled articles.

When there is an accounting for a partially reconciled article, an article event record 122 is generated indicating that the article is now considered scanned out is generated. As part of the step of the process of FIG. 13, in step 312, the server 80 determines whether or not an article event record received is a record indicated that a partially reconciled article should now be considered scanned out. Server 80 performs step 312 by determining if one of records 310 in file 308 is for an article that has the same identification number as the scanned out article. If the evaluation of step 312 tests positive, in step 314 the record 310 for that article is removed from file 308, the file of partially reconciled articles.

If the evaluations of both steps 304 and 312 test negative, than the received record 102 or 122 does not contain information regarding a partially reconciled article. Step 318 represents the conventional processing and storage of the record by the server 80.

The procedure wind-down reconciliation process is the same regardless of whether or not there are partially reconciled articles associated with the patient. If there are partially reconciled articles associated with the patient in the evaluation of step 282, scanner processor 44 compares both the articles scanned into the patient during the procedure and the partially reconciled articles associated with the patient to the articles considered scanned out. Only if both states of each sets of not fully reconciled articles are satisfactorily determined does the scanner processor perform the steps indicating that there has been a satisfactory reconciliation of the articles that need to be so reconciled.

System 30 of this invention provides a means to generate records 102 and 122 of events that occur during the performance of a medical or surgical procedure. These records include records 122 of the use of articles during the procedure. For articles for which reconciliation is important, the system does more than simply generate a record indicating that the article was introduced into the procedure. The records generated by the system for this type of article indicate the current state of the article relative to the procedure. Thus, the system provides a means to determine, while a procedure is progressing, if there are one or more articles associated with the procedure for which reconciliation is required. After the procedure, the records can be used to generate a history of the use of an article from the initial scanning in to the final full reconciliation.

System 30 also provides a means to identify if an article, while currently unreconciled, should be subjected to a later reconciliation. Thus, if the article is intentionally left in the patient, the personnel perform the subsequent procedure on the patient are provided with notice that the article is in the patient and must be subjected to a reconciliation. The data regarding the articles that are to be subjected to a later reconciliation are stored on the central server 80. These data are forwarded to the scanner 40 used in the subsequent procedure on the patient. Thus, system 30 of this invention therefore provides notice of articles used in the previous procedure that need to be reconciled without requiring that a particular single scanner be used on all the procedure associated with a particular patient.

System 30 of this invention does more than provide a means to account for articles. The procedure activity records 102 generated by the system function as a log of events that occur during the procedure as well as the identity individuals involved in the events.

Another feature of system 30 of this invention is that integral with each record 102 and 122 is the identity of the individual that generated the record. These data are useful in the event a question regarding a set of records requires knowledge of the individuals responsible for generating the records.

The event records generated and stored by system 30 of this invention have further uses other than simply being used to maintain records of articles that require reconciliation. There are sometimes instances wherein articles used in medical or surgical procedures are subjected to later recall or are associated with infection events. By retrieving article event records 122 associated with these articles system 30 can be used to identify the patients with whom these articles are associated.

Truncated versions of the article event records 122 can be sent to the billing application 96. Specifically a truncated article event record sent to the billing application may only contain the event identifier 104, the procedure identifier 106 and the article identifier 124. These data are then used by the billing application 96 as input into the generation of the invoice associated with the patient.

Alternative truncated versions of the article event records 122 are sent to the inventory control application 88. The specific version of the record sent to the inventory control application are the version that contains the event identifier and the article identifier 124. The data in these records 122 are used by the inventory control application to determine the current inventory levels of articles used at the facility. The inventory control application compares these inventory levels to target inventory levels for these articles. When an actual inventory level for an article falls below the target level, the inventory control application is employed to facilitate the reordering of the article.

Alternative truncated versions of the article event records can be sent to external implant or product registry databases used to track which items are associated to specific patients.

The article event records 122 can also be used by the inventory control application 88 to assist in the management of the capital articles used in a procedure. Specifically, after the article event records indicate that a particular piece of equipment, for example an anesthesia pump, has been used a set number of times, the inventory control application can be used to generate a notice that the equipment needs to be subjected to a particular level of cleaning and/or preventive maintenance.

Figure 16:
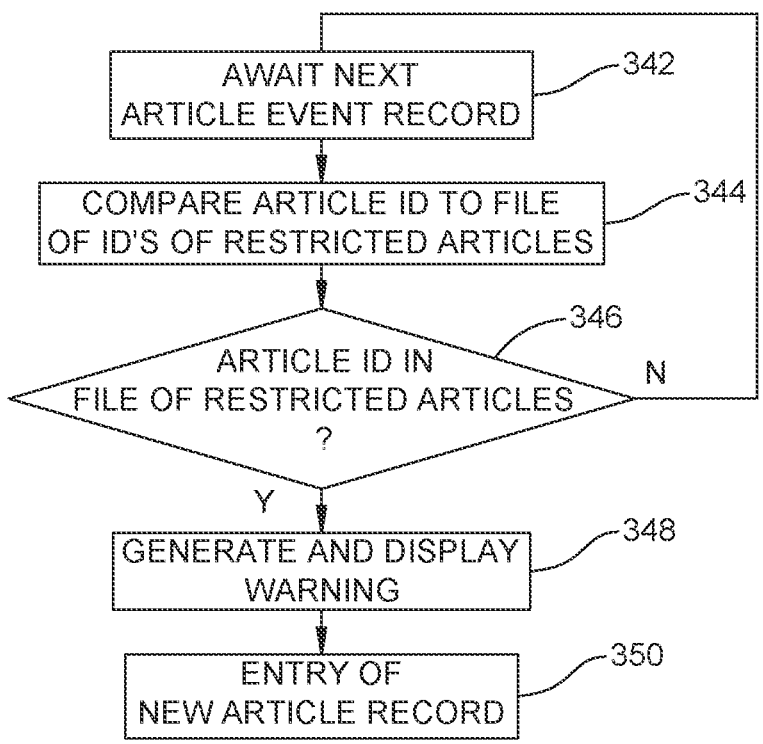
FIG. 16 is a flow chart of how the system of this invention generates warnings regarding articles that may be used as part of a procedure.

Further, after a scanner 40 sends an article event record 122 regarding the use of a particular article to the server, the server may respond with a message regarding the usability of the article. This process is represented by FIG. 16. Step 342 is the server 80 awaiting receipt of an article event record 122. Not shown is the step of the server 80 actually receiving the record. Steps 344 and 346 are the server comparing the identification number for the article to the identification numbers in a file of identification numbers of articles the use of which is restricted. Most likely, the evaluation of step 346 tests false. Few articles are in the file of articles the use of which is restricted. These sub processes run on the server 80 returns to await the next article event record, step 342 is again executed.

There are, however, times when the evaluation of step 346 tests true. The article being scanned into the procedure is on a list of restricted articles. This may be because the article is subject to a recall, the use of the article is passed an expiration date or information obtained elsewhere in the facility indicates the article needs maintenance. Regardless of the reason the article is not usable, step 346 represents the generating of warning by the server 80 that the article is not usable, the receipt of the notice by the scanner 40 and the display of the warning on the scanner display I/O unit 46. For the scanning process to proceed, the scanner processor then requires the scan operator to, in step 330, enter a new article record regarding the article that is subjected to the warning. This record may be an indication that the article is being scanned out of the procedure. Alternatively, it may be decided that given the nature of the warning and the current situation regarding the patient and the procedure, the risks regarding the use of the article are acceptable. If the medical/surgical personnel make this decision, the article event record for the article will be an acknowledgement that the warning was received and a decision was made to proceed with the use of the article.

The event records 102 and 122 generated by system 30 are further be used to evaluate trends that are occurring in a facility. For example by selective retrieval of records, it is possible to determine the number disposable articles different surgeons use when perform the same or similar procedures. These data may reveal that a particular surgeon appears to be using a smaller number of disposable articles than other surgeons performing the same procedure. This cues the staff that this surgeon's methods should be studied so that other surgeons can reduce usage of these articles.

A review of the activity event records 102 may indicate that there is a relatively high number of records indicating that a particular scanner operator attempts to generate article event records for persons or articles that are not on table 140, the table of acceptable identification numbers. If the review indicates that this condition exists it can serve as an indication that this individual may need better training or there is previously unknown fault in the accuracy of the records in table 140.

A review of article event records 122 may indicate there is association between a particular individual and relative high counts of articles that require reconciliation being assigned final states other than scanned out. If the review indicates that this condition exists a study can be undertaken to determine why the condition exists. The server processor can also combine data from stored event records and data retrieved from admissions application 84 to evaluate the percentage of surgical procedures where the scanner is used or whether the scanner was used for a particular procedure.

The event and article data can be analyzed and used include providing evidence that certain articles, procedures, protocols, or other items were or were not used during a procedure or group of procedures.

Data from the servers/scanners used at a number of health care facilities can be aggregated to provide analysis of surgical events across hospital groups and other large collections of facilities. Evaluating this consolidated collection of data allows individuals at one facility to compare events taking place at their facility to events taking place at other facilities. For example, types of comparisons may include: the duration of different types of procedures, the percentage of procedures involving wound-packed articles, the number and type of articles used in procedures, the percentage of procedures where the scanner operator changes during the procedure.

II. Use of Substitute Scanner

During the course of a procedure, the scanner 40 may malfunction. While such malfunctions are rare, this event can occur. A scanner 40 can fail because the battery internal to the scanner is no longer able to provide the charge needed to operate the scanner. A scanner 40 may also fail as a result of being dropped. Regardless of the reason, should such a failure occur, a new scanner 40 may be used to perform the inventory process associated with the procedure.

Figure 17:
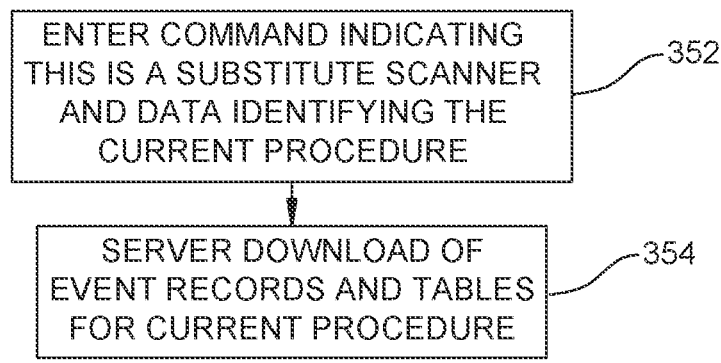
FIG. 17 is flow chart of how a second scanner may substitute for a first scanner during a procedure.

Specifically after a scanner is activated, after step 158 of FIG. 8A, the scanner operator, does not enter a command indicating that new procedure is to begin. In other words, step 164 is not executed. Instead, the scanner operator, as depicted in step 352 of FIG. 17, enters a command indicating that the scanner is a substitute scanner that is to be used as a replacement for a scanner previously used in the procedure. As part of step 352 data regarding this command are transmitted to the server. Integral with these data is an indication of the procedure identification number for the procedure. Alternatively, this data may identify the patient. In response to receipt of this command, the server 80 and scanner collectively execute step 354. In step 354 the server 80, based on the procedure identification number or the identity of the patient contained in the command retrieves the records the server was storing for the procedure. Also in step 354 the server 80 transmits these records to the scanner 40. The scanner 40, also in step 354, stores these records and recreates the tables based on these records in the scanner memory 46.

It is therefore a further feature of system 30 of this invention that, if a scanner 40 employed to generate event records fails, a replacement scanner can be promptly employed without having to, in a record by record basis, recreate in the substitute scanner the files and tables that were stored in the first scanner.

III. Alternative Process for Reconciling Partially Reconciled Articles

Figure 18:
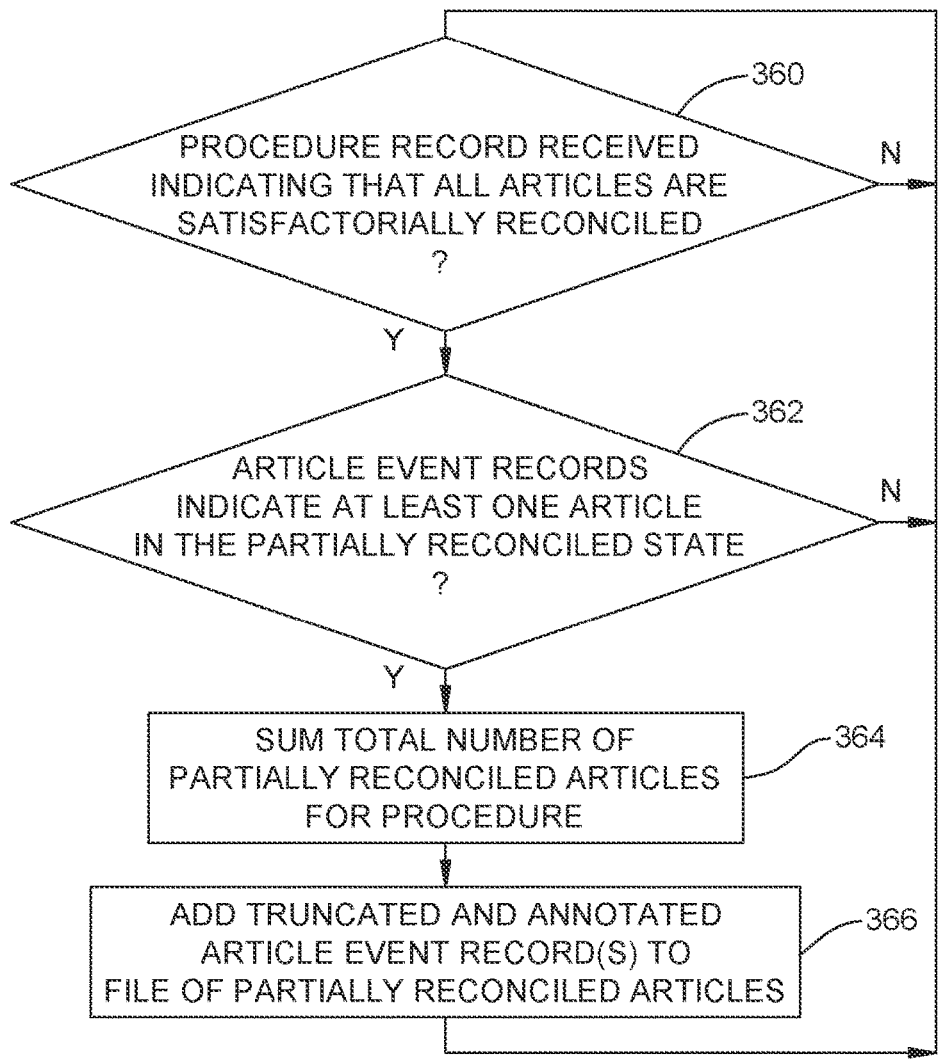
FIG. 18 depicts an alternative means of generating records regarding partially reconciled articles according to this invention.

An alternative means of providing medical and surgical personnel notice that there are partially reconciled articles is now described. In this version of the invention, records are selectively added into the below-described file 370 of partially reconciled articles as each article event record 122 is received by the server 80. In other words, in this version of the invention, the above-described steps 304 and 306 are not executed. This alternative method starts with step 360 of FIG. 18. Step 360 is the processor in the server 80 evaluating whether or not the received procedure event records 102 indicate that, for the procedure, there has been a satisfactory reconciliation of the scanned in articles. Here the satisfactory reconciliation means that for all the newly scanned in articles there are complementary records indicating that the articles should be considered either scanned out or partially reconciled. If the evaluation of step 360 tests negative, the server processor waits for the next procedure event record that indicates there was a satisfactory reconciliation of the scanned in articles.

If the evaluation of step 360 is positive, the server processor reviews the article event records 122 for the procedure in step 362. In step 362 the records 122 are reviewed to determine whether or not for any article 32, the article was classified as being in the partially reconciled state. If the evaluation of step 362 tests negative, since there are no partially reconciled articles, the process of generating records for such articles is terminated. As represented by the loop back to step 360, the server processor waits for the next procedure record from a scanner 40 indicating that, for a procedure, there was a satisfactory reconciliation of all the articles scanned into the procedure.

Figure 19:
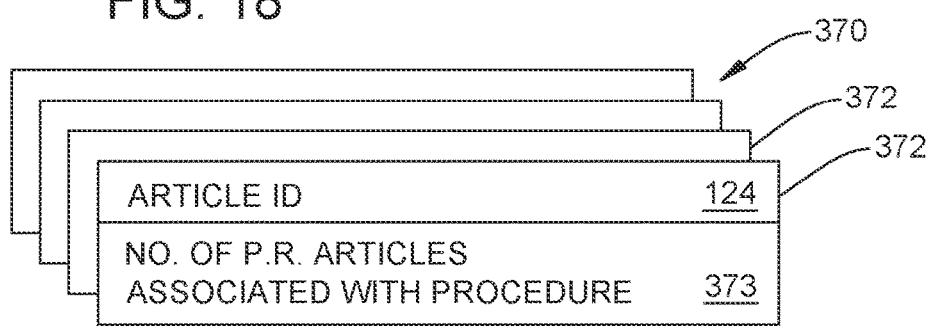
FIG. 19 depicts the contents of a record of a partially reconciled article in an alternative file of partially reconciled articles.

If the evaluation of step 362 tests positive, the server processor sums the total number of partially reconciled articles left in the patient for the procedure, step 364. Step 364 is performed by summing the number of article records generated during the procedure that indicate the current status for the associated article is partially reconciled. In step 366 the server generates records for the partially reconciled articles, records 372, and places the records 372 in a file of partially reconciled articles, file 370 seen in FIG. 19. Each record 372 in file 370 contains two fields of data. The first data are the data in the previously described field 124, the data with the article identifier for the partially reconciled article. The second field, field 373, contains data indicating the total number of partially reconciled articles associated with the procedure. The data in field 373 is the sum generated in step 364.

The loop back from step 366 to step 360 represents that after step 366 is executed the server processor waits for the next procedure record from a scanner 40 indicating that, for a procedure, there was a satisfactory reconciliation of all the articles scanned into the procedure.

During the process of activating a scanner 40, the process of FIGS. 8A and 8B, a copy of the partially reconciled articles file 370, is one of the files sent to the scanner in step 152. In this version of the invention, table 146, the table of reconcilable articles, only contains records of articles that were scanned in during the current procedure. The image 270 only provides count data for the reconcilable articles scanned in during the current procedure.

Figure 20A:
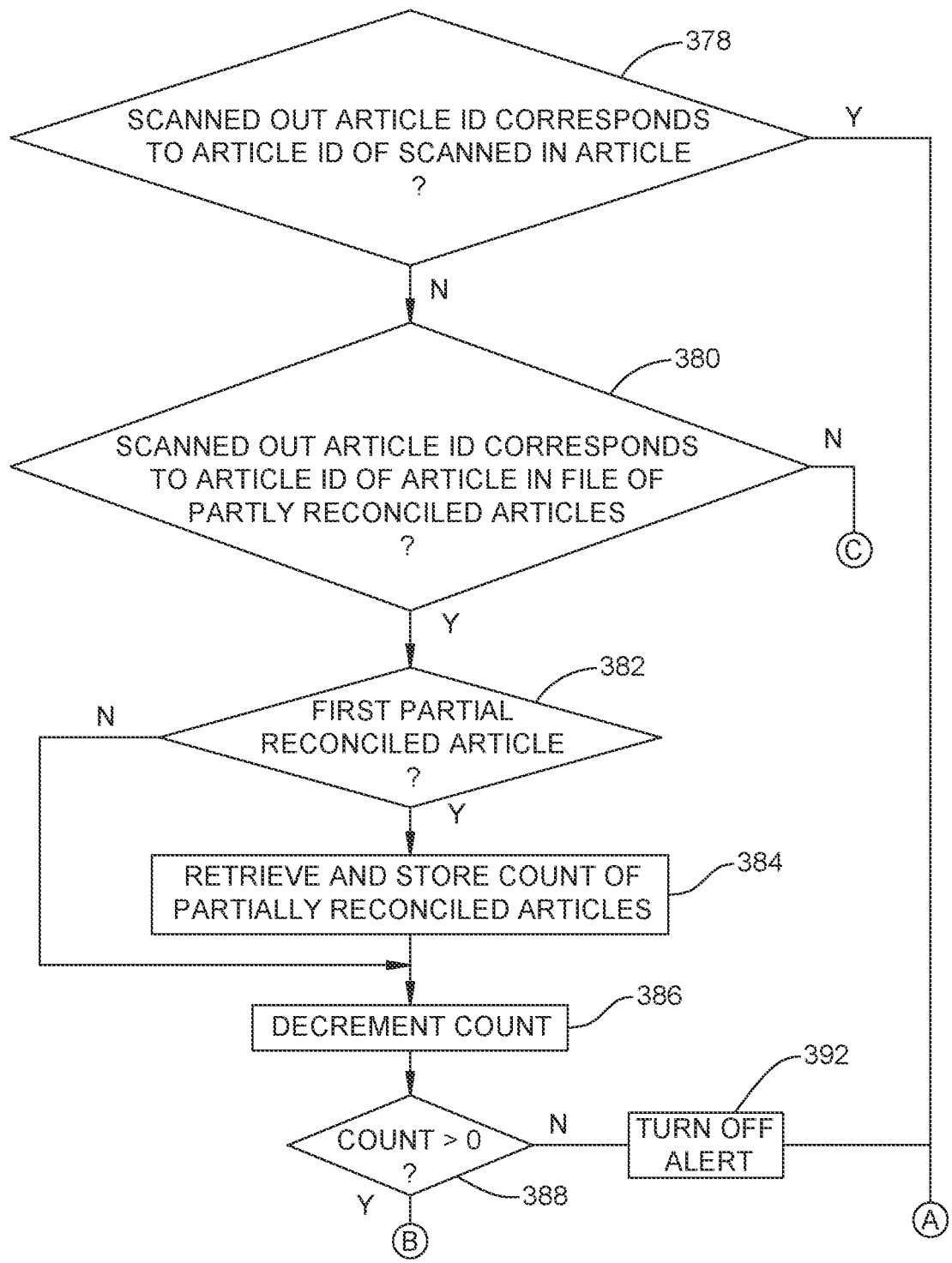
FIGS. 20A and 20B form a flow chart of an alternative process to scan out articles, including partially reconciled articles according to this invention.
Figure 20B:
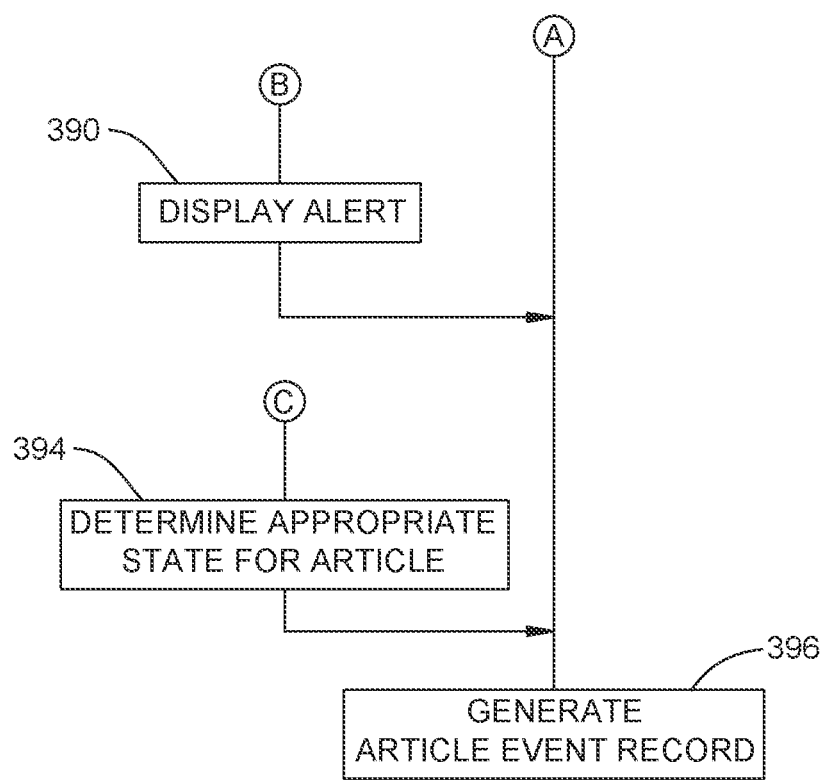

The process of scanning out an article according to this version of the invention is now described by reference to the flow chart of FIGS. 20A and 20B. The steps of these Figures are performed after step 230 of FIG. 10C is executed. More specifically, the steps are executed if, in step 202, the scanner operator indicated that the scan was to scan out the article 32 from the procedure. In this process, step 378 of FIG. 20A is executed. Step 378 is the evaluation to determine if the article identifier for the scanned out article corresponds to one of the article identifiers of articles scanned in during this procedure. These are the articles the identification numbers of which are stored in table 146 in the scanner memory 46. If the evaluation of step 378 tests positive, in step 396 an appropriate article event record 122 is generated. Also as part of step 396 the data in table 146 are also appropriately updated.

If the evaluation of step 378 tests negative, in step 380 the scanner processor compares the article identifier for the scanned out article to the article identifiers in the partially reconciled articles file 370 stored in the scanner memory 46. If the evaluation of step 380 tests positive, the scanned out article is understood to be an article that was scanned in to the patient during a prior procedure and was then classified as being in a partially reconciled state.

If the evaluation of step 380 tests positive, in step 382, the scanner processor 382 determines if this is the first partially reconciled article associated with the patient. This evaluation is performed by reference to the setting of a flag internal to the scanner memory 46. If this evaluation tests positive, in step 384 the scanner processor 44 loads the count number from the field 373 for the record 372 for the partially reconciled article in a field in the scanner memory 46. More specifically, internal to the scanner memory there is a data field that indicates the number of partially reconciled articles associated with the patient undergoing the procedure. Absent the execution of step 384, the value in this field is zero.

If the evaluation of step 382 indicates the scanned out article was not the first partially reconciled article associated with the patient, step 384 is bypassed.

In step 386, the count in the field in which the number of partially reconciled articles associated with the patient is decremented by one. Step 386 is executed regardless of whether the scanned out article was either the first partially reconciled article or a subsequent partially reconciled article.

In step 388 the count in the scanner memory data field of the previously reconciled articles is evaluated. Specifically, the count is evaluated to determine if it is greater than zero. If this evaluation tests positive, then based on the data retrieved from the first partially reconciled article record 372, there are additional partially reconciled articles in the patient. Scanner processor 44, in step 390, therefore causes the display I/O unit to present an alert that these additional partially reconciled articles remain within the patient. The presentation of this alert provides notice to the personnel performing the procedure that these articles most likely need to be reconciled, accounted for, prior to the close of the procedure. It should be understood that during when the second, third and additional evaluations of step 388 test positive, step 390 is the continued presentation of the previously asserted alert.

After the step 390 of asserting or maintained the alert, step 396 is executed. The result of this execution of step 396 results is the generation of an article record indicating that the article 32 once considered partially reconciled is now considered fully reconciled.

During the course of the procedure, there should be an accounting of all the partially reconciled articles. Once there is this accounting, the evaluation of step 388 that is performed after this last article is scanned out should test negative. When this event occurs, in step 392, the scanner processor turns off the alert presented in regard to the partially reconciled articles. After step 390 is performed, step 396 is executed. This particular execution of step 396 results in the generation of the article record indicating that the last partially reconciled article for which there has not been an accounting should now be considered fully reconciled.

There is a possibility that the evaluations of step 378 and 380 will both test negative. This would indicate that, while the article was scanned out of the procedure, it was not scanned in either during the current procedure or a previous procedure. If the article is in this state, step 394 represents the determination by the personnel performing the procedure why, given that the article was never scanned in, is was scanned out. As part of step 394 the personnel determine the state that should be assigned to the article.

Regardless of the result of the evaluation of step 394, the scanner processor performs step 396, an appropriate article event record 122 is generated. When the copy of the article event record is received by the server 80, the server processor still performs step 312. In other words the server processor determines if the received record is a record indicating that a previously partially reconciled article is now scanned out. If the evaluation of step 312 tests positive, the server processor executes a version of step 314. In this execution of step 314 the server processor deletes the record 372 of the partially reconciled article from the partially reconciled article file 370.

Step 396 is also executed after the evaluation of step 394 is performed. An article event record 122 after the execution of step 394 may include an event identifier that the article was simultaneously both scanned into and scanned out of the procedure. Providing article event records with this type of event identifier makes it possible to determine if this type of event is happening with an unusually high frequency. If this type of event occurs at an unusually high frequency at a facility provides an indication that it may be worthwhile to investigate the causes of these events so as to minimize their occurrence.

This version of the system of this invention provides some notice to the persons performing the procedure that there are partially reconciled articles for which an accounting may be required. This version of the invention provides this notice without requiring the scanner memory 48 store large volumes of data or the scanner processor quickly evaluate these larger volumes of data.

In this version of the invention as in the previous version, each scanner 40 has a copy of the partially reconciled articles file 370. Therefore, like the previous version of the invention, this version does not require that to receive notice that there are partially reconciled articles associated with a patient, a single scanner be used as the logging device for all procedures performed on the patient.

IV. Generation of Supplemental Alerts and Post-Operative Analyses

Figure 21:
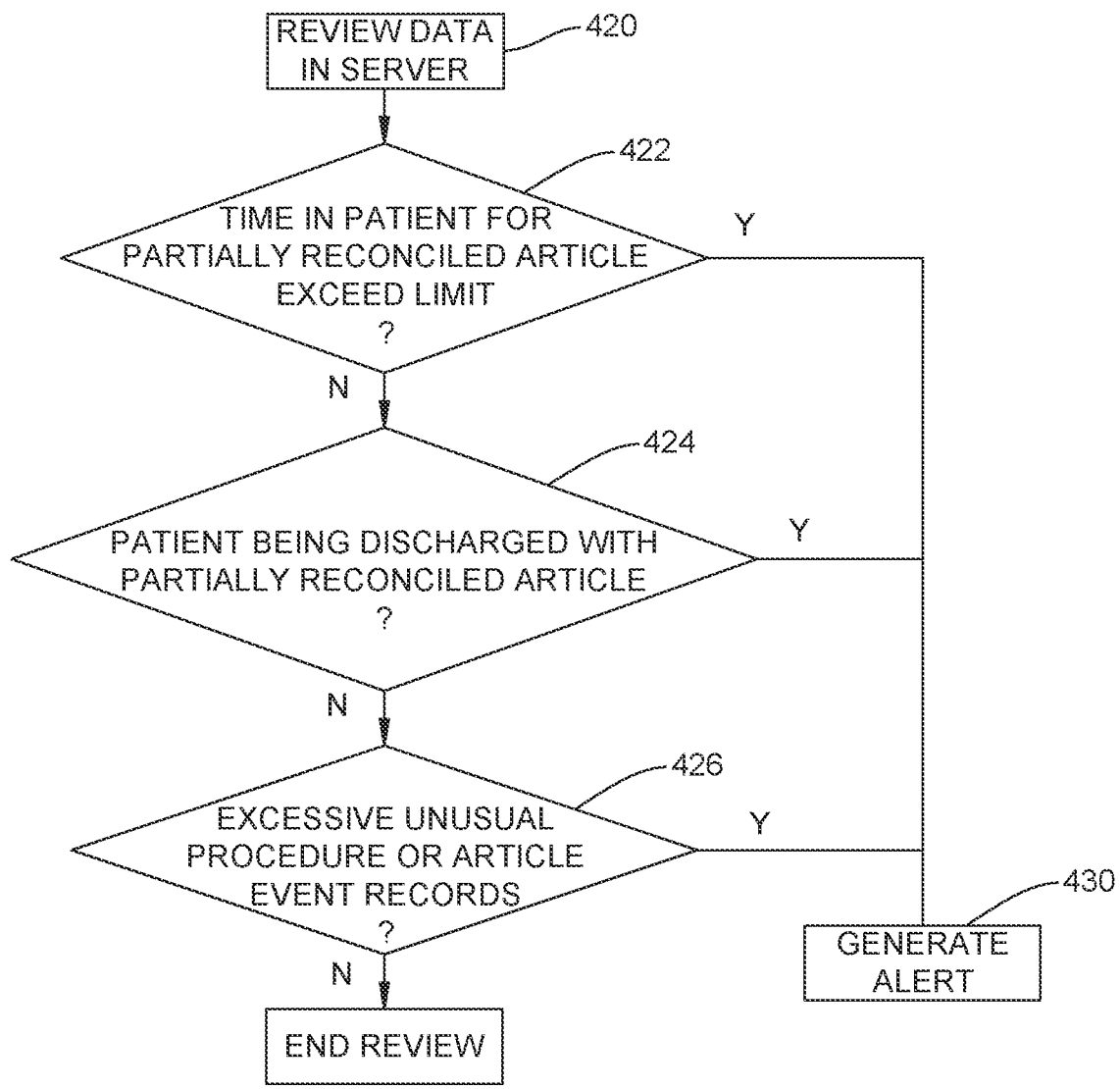
FIG. 21 is a flow chart of how the system of this invention is capable of generating alerts.

System 30 of this invention is further designed to provide additional alerts regarding the partially reconciled articles 32. Step 420 of FIG. 21, is the step of reviewing of the article event records 122 in the server 80. Step 422 is the review of these records based on the current time. This review may indicate that records 122 indicate that an article has been in a patient beyond a predefined time limit. If the server processor determines that one or more articles is in this condition, in step 430 the server processor generates an appropriate alert. This alert, which may be generated based on the admissions application 84 and the data in patient procedure files 170, identifies the patient in which it appears there may be wound packed articles that are overdue for removal.

The server processor and admissions application 84 may collectively generate another review of the article event records when it appears that the patient is getting ready to leave the facility. Specifically notice of this upcoming event is a trigger to, as represented by step 424, evaluate whether or not there may still be wound packed, partially reconciled, articles in the patient. If this evaluation tests positive, in a version of step 430 an appropriate alert is generated.

Step 426 represents the server processor reviewing the procedure and article event records 102 and 122 to determine if there are an excessive number or unusual records associated with a particular individual, procedure, type of article or other common factor. For the purposes of this review an "unusual" records includes but are not limited to: records that indicate during scanning a number of the procedure or article identification number is not acceptable; records indicating that a large number of scanned in articles are later classified in a state other than the scanned out state; records indicating an excessive or abnormally short lapse of time between the start of a procedure and the conclusion of the procedure. Still other reviews may indicate that an unusual event is occurring is that there is a relatively short time between the scanning in of an article and the scanning out of the same article. This may indicate that scanning protocol was not followed and the article was not scanned in prior to the use of the article. Another review that may trigger notice is an indication that the scanner was not used during a procedure. Regardless of the nature of the unusual event (events), once the event (events) is (are) noted in step 426 an appropriate alert can be generated in step 430.

V. Alternative Means of Obtaining Article Identification Numbers

In some versions of this invention, identification numbers associated with an article are not scanned in on an individual article-by-article basis. Some articles 32 are, for example, contained in package that contains plural units of the same article. In a procedure, a single master marker associated with the package may be all that is scanned to scan in all the articles contained in the package. Upon the scanning of this single marker, the scanner generates plural article event records 122, one for each article in the package. If the articles are of the variety for which reconciliation is required, the record 147 in table 146 as is appropriate.

When these plural article event records are generated, each record contains an article identifier unique to the specific article with which the record is associated. These plural unique article identifiers may be from identification article data read from the marker on the package containing the articles.

Alternatively, based on a single unit of identifying data on the package marker, the scanner 40 generates identification data for the individual articles. Thus, based on data in the table of acceptable identification numbers, table 140 that a particular identification number is associated with m number of individual articles, the scanner generates m article event records each with its own identification number. For example, if the data in the table 140 indicates that identification number XXXX-XXXX-XXXX is associated with a package of five sponges, the scanner will generate five article event records 122. The article identification field for these records would contain the following individual identification numbers XXXX-XXXX-XXXX-0; XXXX-XXXX-XXXX-1; XXXX-XXXX-XXXX-2; XXXX-XXXX-XXXX-3; and XXXX-XXXX-XXXX-4.

The above versions of the invention is not limited to assemblies wherein the single identifying marker serves as the root marker for plural articles that are identical to each other. In some versions of the invention, the single marker may be on the outside of a kit or a package that contains all the articles used for a single procedure. Thus once the single marker is scanned, the reference to table 140 provides data that the plural articles associated with marker include: J number of sponges of a first size; K number of sponges of a second size; L number of a first size clip; and M number of vials of a pharmacological compound.

Figure 22:
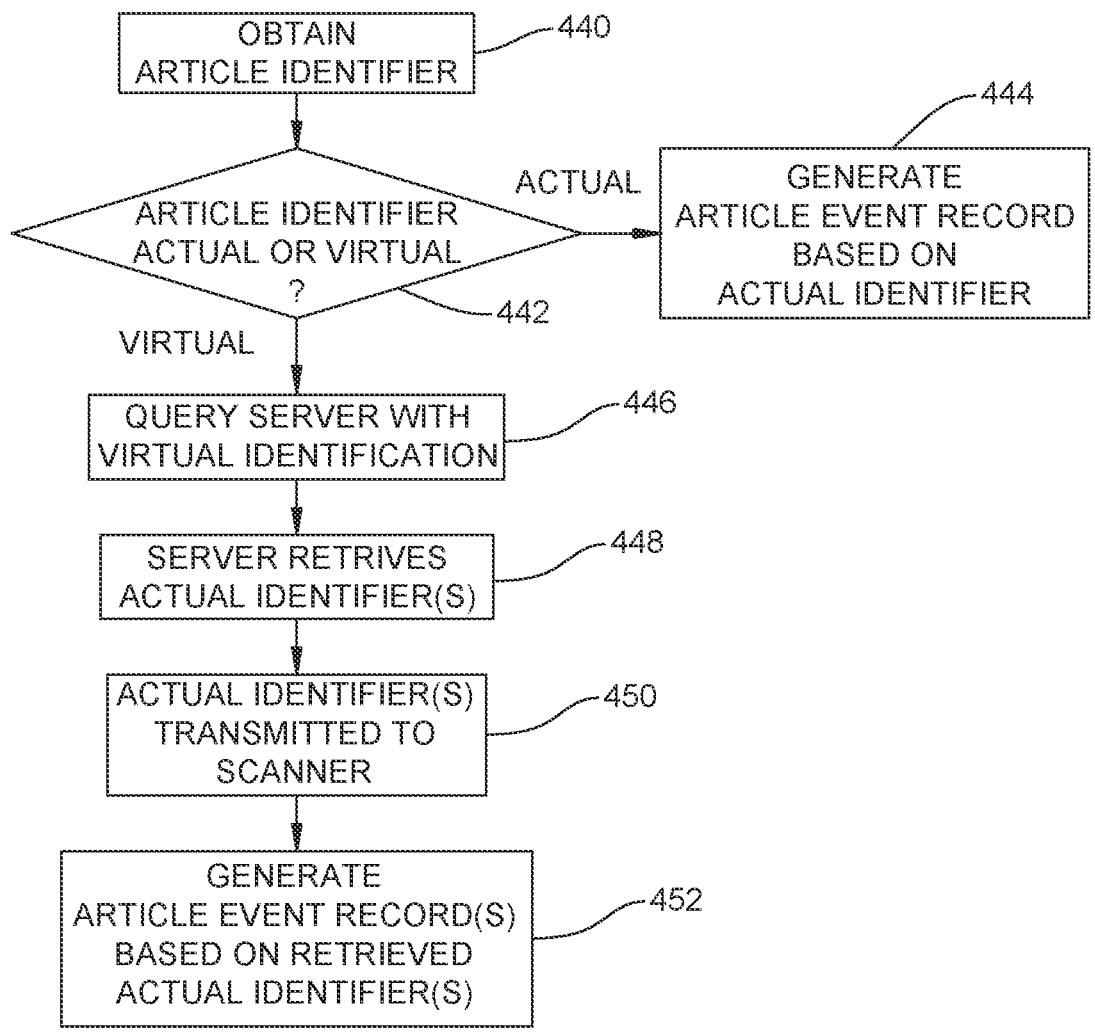
FIG. 22 depicts an alternative means of generating initial article event records according to the system of this invention.

Still another means of obtaining article identification numbers is understood by reference to the flow chart of FIG. 22. Step 440 is the scanning in of the marker on the package. Step 440 is thus the execution of step 224 of FIG. 10C. Step 442 is the scanner processor 44 determining by reference to the setting of the virtual identification flag, the "V" flag, in a record 142 for an article in the table of acceptable identification numbers, table 140. If this evaluation tests negative, than the scanned identification number is used as from the bases of the identification number (or numbers) of the article (or articles) associated with the package, step 444. In this situation, one of the previously described means is used to obtain the article identification number (or numbers) for the article (or articles) associated with the marker.

If the evaluation of step 442 tests positive, the scanner 40, in step 446 sends a query to the server. The query includes the identification data scanned from the marker. In response to this query the server by reference to a table and the identification number determine the actual identification number (or numbers) of the article (or articles) associated with the marker. Step 448 represents the retrieval of the actual identifiers by the server based on the virtual identifier. The transmission of these identification number or numbers to the scanner 40 and the receipt of these numbers by the scanner is represented by step 450. Step 452 represents the scanner based on the identification numbers generating the appropriate number of article event records 122. For example, as a result of the query, ten individual article identification numbers may be forwarded from the server to scanner. In response to the receipt of these ten identification numbers, the scanner generates ten article event records 122. Each record 122 is the record indicating a single one of the ten articles was scanned in. Each record 122 contains a unique one of the ten article identification numbers that was downloaded from the server.

In the above process, the facility server 80 may only serve as a relay between the scanner and the actual data storage unit that stores the tables that relate virtual identification numbers to actual identification numbers. The actual data storage device on which these tables are stored may be remote to the facility at which system 39 is located.

VI. Training Mode

A further feature of system 30 of this invention is that a scanner 40 may be set to not transmit the procedure event records 102 and the article event records 122 generated by the scanner processor to the server 80. When a scanner 40 is set to operate in this state, the scanner is considered to be in a training mode.

In still other versions of the invention, the records 102 and 122 generate during the training mode are forwarded to the server 80. Each of the records generated while the system is in the training mode contains a flag bit that is set to indicate that the record was generated while the system is in the trainings mode. Other processes running on the server detect the presence/absence of this flag bit. If the flag bit is set these processes do not generates alerts that might otherwise be generated. These alerts not generated may include alerts indicating that: the article appears to have been previously used and should not be reused; or the article is overdue for reconciliation.

Placing the scanner in a training mode makes it possible for persons to practice generating records 102 and 122 without being concerned that the records will be stored in the server 80. This makes it possible to use repeatedly use a single set of training articles to practice such record generation without having to be concerned that the data from the server will generate warnings when they are inappropriate to the training situation. It may also be useful for testing the system during the instillation of the system.

VII. Location of Article Marker

Figure 23:
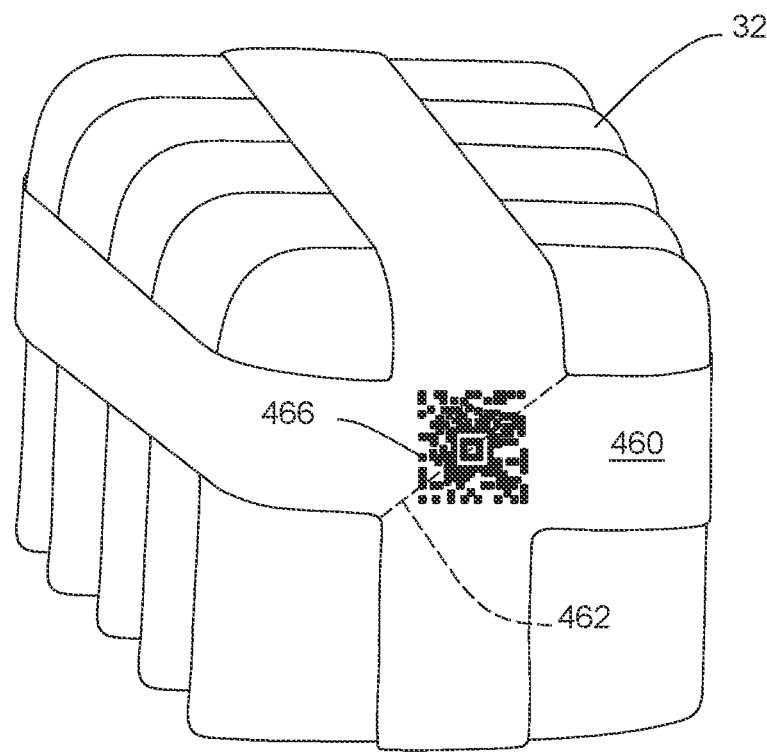
FIG. 23 depicts the placement of a marker on the packing associated with an article according to this invention.

It is a further feature of this invention that the article marker is located on a portion of the packaging associated with the article that is typically separated or broken in order to access the article. In FIG. 23 the articles 32 are sponges. The packaging consists of a paper strip 460 that is wrapped around the sponges. The paper strip 460 is formed with a line of perforations, represented by dots 462. The perforation line is the frangible portion of the strip. The marker is a matrix bar code 466 printed across the perforations.

The placement of the marker at this location suggests that, once the package material is separated or broken to access the articles, the marker is most likely not readable.

The placement of the marker across the section of the packing that is separated or broken serves as cue to the individual responsible for scanning in the articles that the scanning should occur before the package is opened.

VIII. Alternative Embodiments

The above is directed to specific versions of the invention. It should be understood that that different versions of the invention may have features different from what has been described. For example, there is no requirement that all versions of the invention have the features described in association with its version of the invention. Likewise the features of the various versions of the invention may be combined.

Thus some versions of this invention may only be used for generating records of events associated with the articles used in the procedure. Other versions of the invention may only be used to generate records of activities that occur during the procedure.

In FIG. 5 table 140 is shown as having plural records each of which is understood to be associated with a particular range of identification numbers. Here "range" is understood to be more than a list of consecutive ordinal numbers. The same articles for example, may be associated with two sets or identifications numbers that are separated by a set of identification numbers associated with a second type of article. The range of identification numbers should also be interpreted as a version of table 130 wherein the table stores one or more records each being associated with an individual person; location or physical article.

In some versions of the invention, in step 152 one of the files regularly provided to the scanner 40 is table 308, the table of partially reconciled articles. In these versions of the invention, the scanner upon being initialized for a new procedure performs the step 326 of FIG. 15 and extracts the records 310 of the partially reconciled articles for the patient on whom the procedure is being performed. Processor 44 then stores these records as records 147 in the table 146 maintained for the procedure. A benefit of this version of this invention, is that once it is verified that the scanner contains the most current version of file 308, the scanner does not have to wait for a response to a query sent to the server 80.

Likewise, the process shown in FIG. 16 can also be performed by the scanner processor. The file of restricted articles can be distributed by the server to each of the scanners when updates to this file are made. In this way, even if the connection between the scanner and the server is temporarily lost, the scanner can still provide notice that an article is restricted prior to use.

In some versions of the invention, each scanner 40 may not be provided with a copy of file 370 of partially reconciled articles. In these versions of the invention, step 380 may be performed by generating a query to the processor integral with the server 80.

Also, in some versions of the invention, each scanner is not provided with a copy of the file of partially reconciled articles. In these versions of the invention, each scanner maintains a file of the sponges that that scanner was used to classify as being in the partially reconciled state. Unlike the primary versions of the invention, in order to ensure there is a reconciliation of partially reconciled articles, a single same scanner must be used to record all the events associated with the plural procedures that are performed on a patient.

The process steps of the invention may likewise differ from what has been described. Thus, in some versions of the invention, the files described as being provided to a scanner 40 after initialization, may be provided to the scanner at time when the scanner is attached to a dock that provides a conductive link to the server 80. For example, between individual uses of a scanner, a scanner 40 is typically be attached to a charger. The charger, as implied by its name, provides a charging current to the battery that sources the current used to power the other components of the scanner 40. In these versions of the invention, the charger and scanner have complementary data contacts. This is similar to the structure of the rechargeable battery that is the subject of US Pat. Pub. No. US 2007/0090788 A1/PCT Pub. No. WO 2007/050439 A2, the contents of which are explicitly incorporated herein by reference.

In these versions of the invention, the charger is through a network, connected to the server 80. While a scanner 40 is attached to the charger, data are exchanged between the server and the scanner. These data may include the event records 102, 122 generated by the scanner processor during the course of the procedure. Also during these time periods, the server may upload data to the scanner. These data include the current table 140 of acceptable identification numbers or the most current table 308 of partially reconciled articles. In other words, the data uploaded to the scanner 40 in step 152 is uploaded to the processor while the scanner is being charged or otherwise connected to a docking unit.

A benefit of the above versions of the invention the transmission of event records by the scanner to the server may not occur until after the scanner is attached to the charger or similar data docking unit.

A benefit of this version of the invention is that it eliminates the need to rely on the wireless transmission of data between the server 80 and the scanners 40. A further benefit of this version of the invention is the cost of providing bot the scanners 40 and the server with the wireless transceivers required to perform this signal exchange is eliminated. It should therefore be appreciated that for the purposes of this invention the complementary transceivers of the scanners 40 and the server 80 are understood to include components able to facilitate the conductive exchanged of signals between the scanners and the server.

It should further be understood that in the event the wireless communications link between a scanner 40 and the server 80 fails during a procedure, the scanner will continue to operate. The scanner processor will store the records 102 and 122 that would otherwise be sent to the server upon being generated. When the communications link is reestablished, these records 102 and 12 are sent to the server 80.

In some versions of the invention a sub-field of each procedure id field 170 may contain data identifying the patient is associated. This Accordingly, it is an object of the appended claims to cover all variations and modifications that come within the true spirit and scope of this invention.

IX. Clauses

Clause 1. A packaged article assembly for use in a medical or surgical procedure, the assembly comprising: at least one article (32) for use in a medical or surgical procedure; packaging (460) that surrounds the article (32); and a machine readable identifier (466) affixed to one of the article or the package, characterized in that: the package is formed with a frangible section (462) that is broken to access the article (32); and the machine readable identifier is affixed to the package across the frangible section (462) so the breaking of the frangible section prevents the reading of the machine readable identifier.

Clause 2. The packaged article assembly of clause 1, wherein plural articles (32) are contained in the packaging (460).

Clause 3. The packaged article assembly of clause 1 or 2 wherein the at least one article is a sponge.

What is claimed is:

1. A sponge reconciliation system for maintaining records of sponges used during a procedure to ensure proper removal of surgical sponges following the procedure, the sponge reconciliation system including:
    a server;
    a plurality of tablets, each of the plurality of tablets including a processor, a memory, and a transceiver, and wherein each processor is configured to:
        generate a first article record identifying a first sponge scanned into a current procedure, wherein the first article record corresponds to a sponge that is to be considered partially reconciled;
        generate a first procedure event record that identifies a current procedure, a user operating the tablet, and a patient with whom the current procedure is to be identified;
        store data from the first article record on the memory of the tablet, wherein the scanner memory does not contain data that specifically identifies the patients with which the procedure event record and article event record is associated with;
        transmit data from the first procedure event record and the first article record to the server;
        download data from a second article record for a second sponge that has been partially reconciled to the memory of the tablet from the server, the downloaded data being from a prior procedure associated with the patient with which the tablet is currently associated for the current procedure;
    wherein the server is configured to:
        store data received from the first article record and the first procedure event record;
        determine whether the first article event record received is a record indicating that the partially reconciled first sponge should now be considered scanned out;
        based on the step of determining, remove the first sponge from a file of partially reconciled articles;
    and wherein the system is configured to:
        display text associated with a sponge that has been fully counted out in a first color;
        display text associated with a sponge that has not yet been scanned out in a second color; and
        display text associated with a sponge that has been partially reconciled in a third color.

2. The sponge counting system of claim 1, wherein the processors of the tablets and the server are collectively configured so that:
    each processor of the tablet sends a message to the server that identifies the patient with which the processor is currently associated; and
    in response to receipt of the message, the server transmits to the processor of the tablet the records of the partially reconciled sponges associated with the patient with which the tablet processor is associated.

3. The sponge counting system of claim 1, wherein the system is configured to display the status of sponges scanned in to the current procedure with which the tablet is associated and the status of partially reconciled sponges associated with the patient.

4. The sponge counting system of claim 1, wherein the system is configured to display of the number of scanned in sponges scanned in to the current procedure with which the tablet is associated separate from the display of the number of partially reconciled sponges left in the patient.

5. The sponge counting system of claim 1, wherein the system is configured to:
    for a plurality of different types of sponges scanned into the procedure with which the processor of one of the tablets is associated, present on the display for each type of sponge data indicating the number of sponges of that type scanned into the procedure; and
    based on the records for the partially reconciled state sponge associated with the patient with which the processor of the tablet is associated, for each of the different types of partially reconciled sponges, display data indicating the number of sponges of the that type that are in the partially reconciled state, wherein for each type of sponge, the display of the number of sponges scanned into the procedure is separate from the display of the number of partially reconciled sponges of that type.

6. The sponge counting system of claim 1, wherein the plurality of tablets and server include complementary wireless transceivers configured to facilitate the wireless of exchange of signals between the tablets and the server.

7. The sponge counting system of claim 1, wherein: each tablet includes a scanning head configured to read machine readable information that identifies sponges that are scanned by the scanning head; and the processor of the tablet is connected to the scanning head to receive the information that identifies the sponge and to, based on the information, generate the first article record for the sponge, where the generated first article record includes a field with the information that identifies the sponges.

8. The sponge counting system of claim 7, wherein the scanning head is capable of:
    optically reading the machine readable information; or
    reading data from an RFID tag.

9. A sponge reconciliation system for maintaining records of sponges used during a procedure
    to ensure proper removal of surgical sponges following the procedure, the sponge reconciliation system including:

a server;
a plurality of scanners, each of the plurality of scanners being adapted to read identifying data from a sponge; and each of the plurality of scanners including a scanner processor, a scanner memory, and a transceiver, and wherein each scanner processor is configured to:
  generate a first article record identifying a first sponge scanned into a current procedure, wherein the first article record corresponds to a sponge that is to be considered partially reconciled;
  generate a first procedure event record that identifies a current procedure, a user operating the scanner, and a patient with whom the current procedure is to be identified;
  store data from the first article record on the scanner memory, wherein the scanner memory does not contain data that specifically identifies the patients with which the procedure event record and article event record is associated with;
  transmit data from the first procedure event record and the first article record to the server;
  download data from a second article record for a second sponge that has been partially reconciled to the scanner memory from the server, the downloaded data being from a prior procedure associated with the patient with which the scanner is currently associated for the current procedure;
wherein the server is configured to:
  store data received from the first article record and the first procedure event record;
  determine whether the first article event record received is a record indicating that the partially reconciled first sponge should now be considered scanned out; and
  based on the step of determining, remove the first sponge from a file of partially reconciled articles.

10. The sponge counting system of claim 9, wherein the scanner processors and the server are collectively configured so that:
each scanner processor sends a message to the server that identifies the patient with which the scanner processor is currently associated; and
in response to receipt of the message, the server transmits to the scanner processor the records of the partially reconciled sponges associated with the patient with which the scanner processor is associated.

11. The sponge counting system of claim 9, wherein the system is configured to display the status of sponges scanned in to the current procedure with which the scanner is associated and the status of partially reconciled sponges associated with the patient.

12. The sponge counting system of claim 9, wherein the system is configured to display of the number of scanned in sponges left in the patient separate from the display of the number of partially reconciled sponges left in the patient.

13. The sponge counting system of claim 9, wherein system is configured to:
for a plurality of different types of sponges scanned into the procedure with which the scanner processor is associated present on the display for each type of sponge data indicating the number of sponges of that type scanned into the procedure; and
based on the records for the partially reconciled state sponge associated with the patient with which the scanner processor is associated, for each of the different types of partially reconciled sponges, display data indicating the number of sponges of that type that are in the partially reconciled state, wherein for each type of sponge, the display of the number of sponges scanned into the procedure is separate from the display of the number of partially reconciled sponges of that type.

14. The sponge counting system of claim 9, wherein the plurality of scanners and server include complementary wireless transceivers configured to facilitate the wireless of exchange of signals between the scanners and the server.

15. The sponge counting system of claim 14, wherein:
each scanner includes a scanning head configured to read machine readable information that identifies sponges that are scanned by the scanner; and
the scanner processor is connected to the scanning head to receive the information that identifies the sponge and to, based on the information, generate the first article record for the sponge, where the generated first article record includes a field with the information that identifies the sponges.

16. The sponge counting system of claim 9, wherein the system is configured to:
display text associated with a sponge that has been fully counted out in a first color; and
display text associated with a sponge that has been partially reconciled in a second color.

17. A sponge reconciliation system for maintaining records of sponges used during a procedure to ensure proper removal of surgical sponges following the procedure, the sponge reconciliation system including:
a server;
a plurality of tablets, each of the plurality of tablets including a processor, a memory, and a transceiver, and wherein each processor is configured to:
  generate a first article record identifying a first sponge scanned into a current procedure, wherein the first article record corresponds to a sponge that is to be considered partially reconciled;
  generate a first procedure event record that identifies a current procedure, and a patient with whom the current procedure is to be identified;
  store data from the first article record on the scanner memory, wherein the scanner memory does not contain data that specifically identifies the patient with which the procedure event record and article event record is associated with;
  transmit data from the first procedure event record and the first article record to the server;
  download data for a second article record for a second sponge that has been partially reconciled to the memory from the server, the downloaded data being from a prior procedure associated with the patient with which the tablet is currently associated for the current procedure;
and wherein the system is configured to:
  display text associated with a sponge that has not yet been scanned out in a first color; and
  display text associated with a sponge that has been partially reconciled in a second color.

18. The sponge counting system of claim 17, wherein the processors of the tablets and the server are collectively configured so that:
each processor of the tablets sends a message to the server that identifies the patient with which the processor is currently associated; and
in response to receipt of the message, the server transmits to the processor of the tablet the records of the partially reconciled sponges associated with the patient with which the tablet processor is associated.

19. The sponge counting system of claim 17, wherein the system is configured to display the status of sponges scanned in to the current procedure with which the tablet is associated and the status of partially reconciled sponges associated with the patient.

20. The sponge counting system of claim 17, wherein the system is configured to display the number of scanned in sponges left in the patient separate from the display of the number of partially reconciled sponges left in the patient.

\* \* \* \* \*